(12) United States Patent
Rodriguez Albalat et al.

(10) Patent No.: US 9,201,066 B2
(45) Date of Patent: Dec. 1, 2015

(54) RAPID PROCESS FOR DETECTION OF MICROORGANISMS WITH MAGNETIC PARTICLES

(75) Inventors: Guillermo Rodriguez Albalat, Vila Real (ES); Maria Luisa Jimenez Bono, Valencia (ES); Daniel Canos Marti, Castellon (ES)

(73) Assignee: BIOTICA, BIOQUIMICA ANALITICA, S.L., La Plana (ES)

( * ) Notice: Subject to any disclaimer, the term of this patent is extended or adjusted under 35 U.S.C. 154(b) by 0 days.

(21) Appl. No.: 13/295,937

(22) Filed: Nov. 14, 2011
(Under 37 CFR 1.47)

(65) Prior Publication Data
US 2013/0011862 A1 Jan. 10, 2013

Related U.S. Application Data

(63) Continuation of application No. 13/120,479, filed as application No. PCT/ES2008/000613 on Sep. 26, 2008, now abandoned.

(51) Int. Cl.
| | |
|---|---|
| *A61K 39/00* | (2006.01) |
| *C12Q 1/00* | (2006.01) |
| *G01N 33/53* | (2006.01) |
| *G01N 33/543* | (2006.01) |
| *G01N 33/569* | (2006.01) |

(52) U.S. Cl.
CPC ........ *G01N 33/54346* (2013.01); *G01N 33/569* (2013.01)

(58) Field of Classification Search
USPC .......... 424/130.1, 150.1, 163.1, 164.1, 178.1, 424/234.1; 435/4, 7.1, 7.2, 7.72, 29; 436/526
See application file for complete search history.

(56) References Cited

U.S. PATENT DOCUMENTS

| | | |
|---|---|---|
| 4,000,060 A | 12/1976 | Collin |
| 5,183,638 A | 2/1993 | Wakatake |
| 6,562,209 B1 | 5/2003 | Sullivan et al. |
| 2003/0049171 A1 | 3/2003 | Tamura et al. |
| 2006/0292555 A1 | 12/2006 | Xu et al. |
| 2007/0199901 A1 | 8/2007 | Campagnolo et al. |
| 2007/0231833 A1 | 10/2007 | Arcidiacono |

FOREIGN PATENT DOCUMENTS

| | | |
|---|---|---|
| EP | 0 030 086 A1 | 6/1981 |
| EP | 0 498 920 A2 | 8/1992 |
| EP | 0 605 003 A2 | 7/1994 |
| WO | 2005/059085 A2 | 6/2005 |
| WO | 2006/091630 A2 | 8/2006 |

OTHER PUBLICATIONS

Peter Irwin, et al., "Blocking nonspecific adsorption of native food-borne microorganisms by immunomagnetic beads with l- -carrageenan", Carbohydrate Research, Feb. 25, 2004, pp. 613-621, vol. 339, No. 3.

Andrew G. Gehring, et al., "Enzyme-linked immunomagnetic chemiluminescent detection of *Escherichia coli* 0157:H7", Journal of Immunological Methods, Oct. 1, 2004, pp. 97-106, vol. 293, No. 1-2.

*Primary Examiner* — Rodney P Swartz
(74) *Attorney, Agent, or Firm* — Sughrue Mion, PLLC

(57) ABSTRACT

The present invention relates to processes for the rapid detection, semi-quantification and quantification of live microorganisms in solutions or suspensions using immunomagnetic particles, without requiring pre-enrichment through culture of the microorganism. The invention also relates to kits for carrying out said processes and to the quantification of the microorganisms detected by means of automated biosensor equipment.

31 Claims, 8 Drawing Sheets

| Absorbance 550 nm | Concentration of Legionella (cfu/L) |
|---|---|
| less than 0.04 | less than $10^3$ |
| 0.04-0.07 | $10^3$ |
| 0.07-0.20 | $10^4$ |
| 0.20-0.60 | $10^5$ |
| 0.60-1.90 | $10^6$ |
| more than 1.90 | more than $10^6$ |

FIG. 8

| Culture value (cfu/L)[1] | Quantitative result (cfu/L)[2] | Qualitative result (+/−)[3] |
|---|---|---|
| 0 | 0 | − |
| $2.0 \times 10^2$ | 0 | − |
| $2.9 \times 10^3$ | $3.7 \times 10^3$ | + |
| $1.9 \times 10^4$ | $3.6 \times 10^4$ | + |
| $5.0 \times 10^5$ | $6.9 \times 10^5$ | + |

[1] ISO 11731:1998 method (plate culture), n=15.
[2] quantitative method based on the invention, n=15.
[3] qualitative method based on the invention, n=15

FIG. 9

| Concentration of Escherichia coli (cfu/ml) | Absorbance 405 nm | |
|---|---|---|
| | A | B |
| 0 | 0.09 | 0.15 |
| 10 | 0.15 | 0.36 |
| $10^3$ | 0.18 | 0.45 |
| $10^5$ | 0.18 | 0.81 |

A covalently bound dextran-aspartic acid-aldehyde polymer
B bovine serum albumin adsorbed, maintaining its concentration in excess throughout the analysis

FIG. 10

Protective effect of the pressure of blocking agent (bovine serum albumin) on the magnetic particle, maintained throughout the analysis, to attenuate the non-specific adsorption of the reading molecule reading reaction kinetics (Absorbance at 405 nm)

| t (min) | initial blocking [a] | permanent blocking [b] | reduction of the non-specific signal (%) |
|---|---|---|---|
| 0 | 0.00 | 0.00 | 0.00 |
| 1 | 0.28 | 0.07 | 75.0 |
| 2 | 0.52 | 0.16 | 69.0 |
| 3 | 0.72 | 0.21 | 71.0 |

[a] 25 µl of anti-*E. coli* magnetic particle blocked before the mixing with a sample without bacterium.

[b] 25 µl of anti-*E. coli* magnetic particle blocked before the mixing with a sample without bacterium, with the blocking pressure maintained throughout the analysis, except in the incubation with the antibody conjugated with the reading molecule (peroxidase)

FIG. 11

| Concentration of *Legionella* (cfu/L) | |
|---|---|
| 0 | $10^3$ |
| $0.07^A$ | $0.13^A$ |
| $0.06^B$ | $0.25^B$ |

$^A$ One capture
$^B$ Three successive captures

FIG. 12

| Absorbance 550 nm | | |
|---|---|---|
| | a | b |
| Control$^1$ | 0.06 | 0.08 |
| Sample$^2$ | 0.14 | 0.40 | a 15-minute immunocapture step
b 16-hour immunocapture step
$^1$ 0 cfu/L
$^2$ $10^4$ cfu/L

FIG 13

| Live *Legionella* | | Dead *Legionella* | |
|---|---|---|---|
| concentration (cfu/L) | absorbance 550 nm | concentration (cfu/L) | absorbance 550 nm |
| $1.95 \times 10^5$ | 0.63 | $4.97 \times 10^6$ | 0.0 |
| $5.0 \times 10^4$ | 0.24 | $4.97 \times 10^5$ | 0.0 |
| $1.95 \times 10^4$ | 0.10 | $4.97 \times 10^4$ | 0.0 |
| $5.0 \times 10^3$ | 0.05 | $4.97 \times 10^3$ | 0.0 |

FIG. 14

Concentration of *Legionella* (cfu/L)

| Origin of sample | PCR | Culture | Signal |
|---|---|---|---|
| Cooling towers | 0 | 0 | 0 |
| | 3.93E+06 | 2.50E+05 | 0.02 |
| | 2.64E+07 | 2.50E+06 | 0.05 |
| | 4.63E+08 | 2.50E+07 | 0.21 |
| Waste water | 0 | 0 | 0 |
| | 3.93E+06 | 2.50E+05 | 0 |
| | 2.64E+07 | 2.50E+06 | 0.03 |
| | 4.63E+08 | 2.50E+07 | 0.16 |

US 9,201,066 B2

RAPID PROCESS FOR DETECTION OF MICROORGANISMS WITH MAGNETIC PARTICLES

This is a continuation of Application No. 13/120,479 (now abandoned) filed Mar. 23, 2011, which is the National Stage of PCT/ES2008/000613 filed Sep. 26, 2008; the above noted prior applications are all hereby incorporated by reference.

TECHNICAL FIELD OF THE INVENTION

The present invention relates to processes for the rapid detection, semi-quantification and quantification of live microorganisms in solutions or suspensions using immunomagnetic particles, without requiring pre-enrichment through culture of the microorganism. The invention also relates to kits for carrying out said processes and to the quantification of the microorganisms detected by means of automated biosensor equipment.

BACKGROUND OF THE INVENTION

Microbial contamination has severe consequences for human and environmental health, not only due to its effect on health care and prevention, but also due to its long-reaching financial impact (Hutton G, Bartram J, "Global costs of attaining the Millennium Development Goal for water supply and sanitation", Bulletin of the World Health Organization, 86(1): 13-9, 2008). Bacteria, viruses, yeasts and protozoa are causal agents of an extraordinary number of diseases.

These infectious microorganisms are biological agents which reach their hosts through supports serving as a carrier, they are established in the body of their host and cause damage. According to the present invention, a microorganism is a prokaryotic or eukaryotic microscopic organism, not including viruses.

Bacteria fundamentally include those known as pathogenic bacteria, such as, for example, species of *Enterobacteriaceae, Vibrionaceae, Bacillus, Escherichia, Streptococcus, Pseudomonas, Salmonella, Legionella, Enterobacter*, etc.

Bacteria can spread to vertebrates by different methods, specifically through foods (for example, *Salmonella*), contaminated beverages (for example, *Escherichia coli*) or in droplets which can be transmitted by air (for example, *Legionella*). Thus, their absence in places such as cooling towers, water conduits in hospitals and hotels, public buildings such as schools, swimming pools, gymnasiums, resorts, spas, and the like, must be regularly checked. The process of the present invention will generally be applied to pathogenic bacteria.

These supports can contain the infectious microorganism, which causes the damage or disease, for a time sufficient to allow even the proliferation thereof, such that in only a few hours or days an infective concentration can be reached, above which it is highly likely that the host will be reached and damage will be caused.

It is obvious that it is necessary to detect the presence and concentration of the causal biological agent in these supports, which serve as a carrier for it in order to reach the host, for the purpose of establishing a correct prevention of the associated environmental and health risks. In particular, the rapid obtaining of results and the simplicity of the process for determining the presence and concentration thereof enables two fundamental issues for defining an efficient prevention and control strategy: 1) increasing the analysis frequency with a low and affordable cost facilitating the industrial application thereof; and 2) performing the analysis in situ in a short time, to prevent infective concentrations sustained over time and minimize the probability of the diseases, allowing appropriately applying corrective measures. This enables the integration of the analysis in routine monitoring and control operations of the risk environments.

The traditional methods for the detection and enumeration of microorganisms are slow and complex, therefore they require qualified personnel for performing several steps of handling (Noble R T, Weisberg S B. "A review of technologies for rapid detection of bacterium in recreational waters". Journal of Water and Health, 3(4):381-92, 2005; Gracias K S., McKillip J L., "A review of conventional detection and enumeration processes for pathogenic bacterium in food", Canadian Journal of Microbiology, 50(11):883-90, 2004; Rompré A., Serváis P., Baudarts J., de-Roubin M R., Laurent P., "Detection and enumeration of coliforms in drinking water: current processes and emerging approaches", Journal of Microbiological Processes, 49(1):31-54, 2002). The standard method comprises isolating and counting the colonies of the bacterium grown under certain culture conditions. It also has serious limitations for performing a correct prevention of the risk associated with the microorganism, among others, the following: 1) the concentration of the microorganism which is to be determined in the samples can be low, and can furthermore be accompanied by other different microorganisms (microbiota). Consequently, it may be necessary to separate the microbiota before inoculating the culture media. Otherwise, said microbiota can compete favorably in the culture medium, and proliferate until masking or preventing the growth of the microorganism which is to be determined; and 2) the time required from the sampling until obtaining the count is generally greater than the time necessary for the microorganism to be duplicated, by several hours, and in some cases even by several days or weeks. This time is even significantly greater than the time which the microorganism may require to reach an infective concentration. Therefore, it is necessary to be able to detect the microorganism in the sample in a short time, for example approximately in 1 hour.

These limitations have promoted the development of other alternative methods. In particular, the use of recognition biomolecules, such as antibodies, antigens and nucleic acids, immobilized on a wide variety of supports (solid phase), is very interesting for the development of immunoassays in the environmental, food, biomedical, industrial and analytical chemistry field.

Some methods have been developed to substitute traditional techniques, such as, for example, immunoassays and PCR (polymerase chain reaction) techniques, which in addition to being slightly more rapid, are quite specific and sensitive.

Immunoassays, based on the antigen-antibody reaction, have recently been developed, which are commonly used to detect disease-causing pathogenic microorganisms (Meer R R, Park D L., "Immunochemical detection methods for *Salmonella* spp., *Escherichia coli* O157:H7, and *Listeria monocytogenes* in foods", Reviews of environmental contamination and toxicology, 142:1-12, 1995). However, these methods have serious drawbacks. The following stand out among such drawbacks:

1) A negative result does not rule out the presence of the microorganism in the analyzed sample, since the microorganism could be at concentrations lower than the limit of detection of the method. Therefore, in immunoassays, including those of the ELISA (enzyme-linked immunosorbent assay) type, a minimum concentration of $10^5$-$10^6$ cells is required for the detection of the microorganism, in a limited assay volume generally between 0.1 and 1.0 ml. This limit is highly conditioned because these methods do not allow using large volumes of sample since many commercially available immunoassays require a minimum concentration of cells of the microorganism for the detection, which makes it necessary to pre-enrich the sample and consequently significantly increase the assay time, necessary to reach a sufficient cell concentration of the microorganism which is to be determined.

2) Furthermore, the method does not distinguish between live or dead bacteria, because the free antigen is also detected, and because after the application of biocidal treatments false positives could be obtained due to the presence of dead bacteria or of the free antigen.

3) The limit of detection of the assay depends to a great extent on the microbioligical and chemical composition of the sample, because the presence of certain chemical compounds or of enzymatic activities of other microorganisms or even of the microorganism which is to be analyzed itself, can interfere in the detection and quantification of the latter.

Another set of techniques, the mentioned PCR techniques, are based on the amplification of a specific fragment of the genome of the microorganism. The nucleic acids of a sample are extracted and purified, to then be enzymatically amplified (by means of the polymerase enzyme) in cycles, and developed by means of electrophoresis or labeling with fluorescent probes. The main limitations of these methods are the high variability shown by the results depending on the matrix analyzed (Yaradou D F, Hallier-Soulier S, Moreau S, Poty F, Hillion Y, Reyrolle M, André J, Festoc G, Delabre K, Vandenesch F, Etienne J, Jarraud S. "Integrated real-time PCR for detection and monitoring of *Legionella pneumophila* in water systems", Applied Environmental Microbiology, 73 (5): 1452-6, 2007; Joly P, Falconnet P A, André J, Weill N, Reyrolle M, Vandenesch F, Maurin M, Etienne J, Jarraud S., "Quantitative real-time *Legionella* PCR for environmental water samples: data interpretation", Applied Environmental Microbiology, 72 (4):2801-8, 2006), and on the process for preparing the sample before the extraction of the nucleic acids, and in addition, on the large variety of inhibitors of the polymerase enzyme, which may be present in the samples.

A patent document representative of the analysis of bacteria in liquid samples by means of PCR is WO 01/40505 A1. Said document describes an analysis process for the presence of *Legionella* with an immunocapture step, and mentions that the main advantage of detecting *Legionella* by PCR is that it needs 24 to 48 h if the analysis is carried out by this method, in comparison with the traditional method of culture which needs 10 to 15 days to obtain the results. In said document, the bacteria can be captured by means of supports activated with antibodies, and it mentions the possibility of using magnetic beads, to then break the cells and extract the DNA, for the purpose of performing a PCR. It is therefore a method which requires breaking the integrity of the microorganism and which is subject to the known drawbacks of the PCR. The invention also relates to a kit for carrying out the method.

There is currently no universally accepted method for the preparation of the sample which allows obtaining reproducible results in all types of samples by means of the PCR technique, therefore it is necessary to continue developing new methods for the removal of inhibitors of the reaction and which simultaneously allows an efficient recovery of the microorganism.

Another option is the immunocapture of the microorganism which is to be determined, by means of using paramagnetic particles or spheres coated with antibodies directed against antigens of the microorganism in question. These immunomagnetic particles are mixed with the sample, form immunocomplexes with the specific microorganism, and allow separating and concentrating the captured microorganisms by means of applying a magnetic field, removing other components from the sample which can interfere with the determination.

For example, the use of an immunomagnetic separation by means of superparamagnetic particles or spheres coated with antibodies directed against antigens of the microorganism of interest, in combination with the real-time PCR technique, has been described (Yáñez M A, Carrasco-Serrano C, Barbera V M, Catalán V. "Quantitative detection of *Legionella pneumophila* in water samples by immunomagnetic purification and real-time PCR amplification of the dotA gene", Applied Environmental Microbiology, 71 (7):3433-41, 2005), but the recovery rate of the microorganism and the reproducibility of the capture thereof decrease with the increase of the complexity of the analyzed water.

The techniques for increasing the sensitivity of immunosorption assays have been focused on increasing the efficiency of the transduction of the signal, by means of using more efficient reading molecules and better detectors (L. J. Kricka, "Selected strategies for improving sensitivity and reliability of immunoassays", Clinical Chemistry, Vol 40, 347-357, 1994). These techniques have involved the reduction of the pre-enrichment time of the sample, although not below 8 hours, and the limit of detection is at $10^6$ cfu/l. For example, in order to increase the sensitivity of the method for the immunocapture of the microorganisms, several methods are applied, such as document US 2005/0202518 A1, for example, which applies immunomagnetic microspheres in the immunocapture step, but after a culture pre-enrichment step for 8-15 hours.

Patent document US 2006/0246535 A1 describes the detection of microorganisms in solution or dispersion, without pre-enrichment, using latex microspheres coated with antibodies, subsequently detecting the microorganism by means of measuring the agglutination.

Document ES 2 237 272 A1 describes a process for detecting and quantifying antibodies specific for *Legionella pneumophila* in sexological samples, by means of the agglutination-sedimentation of latex particles sensitized with an antigen of *L. pneumophila*. It also describes the method for obtaining sensitized latex particles and the reaction buffer in which the immunoreaction takes place.

Some patents intend to increase the sensitivity of the detection of microorganisms by means of using magnetic nanoparticles versus magnetic microparticles (1 µm=1000 nm). For example, patent US 2006/292555 A1 indicates that "there are, to date, no general and satisfactory assays that can detect bacteria at concentrations of <$10^2$ colony forming units per milliliter (cfu/ml) without pre-enriching the bacteria via a culture process". Explicitly, the mentioned patent states that the sensitivity achieved, of the order of 10-100 bacteria/ml, cannot be achieved by means of microparticles, understanding as such those the diameter of which is in the order of one micron, not of one nanometer. Thus, said patent document describes a method for detecting pathogens which comprises using magnetic nanoparticles formed by an antibiotic, the vancomycin bound to the surface of FePt (iron-platinum) nanoparticles.

There are several documents the method of which comprises the magnetic attraction of the particles on a solid support. For example, patent documents U.S. Pat. Nos. 5,834,197 and 6,159,689, both of the same authors, describe methods for capturing and labeling a species, which consists of the attraction of particles having affinity for the species sought. The method comprises the magnetic attraction of said particles on a solid support by magnetic forces, and being immobilized, thus forcing the circulation of the sample and making it pass through the support. On one hand, it is evident that the number of favorable collisions for an antigen-antibody interaction will be smaller because the particles are fixed in a support, and part of the surface covered with antibodies is not accessible, and on the other hand, the exposed area is always the same and only a fraction of the area is actually available, such that the steric hindrance due to the initially captured bacteria limits the efficiency of new collisions very soon. This loss of effective area is not only due to the permanent contact with the support, but also to the aggregation of the particles, which is favored when they are retained on the support and are very close to one another, which increases this loss of efficiency even further. Furthermore, the same sample is repeatedly recirculated through the support with the retained particles; therefore there is no possibility of refreshing the sample in loads, but rather a single load of sample per recirculation is used up.

Document WO 02/101354 A2, which relates to kits and methods for the detection of microorganisms in a sample, also describes a method which comprises adhering capture antibodies specific for a marker of the microorganisms to a solid support; followed by adding second antibodies which may be conjugated to a molecule denoting the presence of the microorganisms, preferably by means of light which can be detected.

Document ES 2 208 121 A1 also relates to a method for the identification and quantification of analytes in which the antibodies and the antigens are immobilized, but instead of on a solid support as in WO 02/101354 A2, U.S. Pat. Nos. 5,834, 197 and 6,159,689, on magnetic silica particles which are used as biosensors. The magnetic particles of the invention are iron oxide nanoparticles obtained by the Massart method, with a size of 5 to 30 nm, coated by a silica layer with a thickness of 30 to 100 nm.

The abstract of the document WO 2006/123781 A1 also relates to the use of magnetic silica particles in methods for recovering a microorganism from a sample, for which the sample is contacted with the particles absorbing it. The particles are characterized in that they have a diameter of 6 μm or less and their specific surface area is 50 $m^2$/g or less.

Document US 2006/0211061 A1 relates to methods for the rapid detection of pathogenic microorganisms in a fluid by means of immunoassays. The method consists of binding a magnetic microparticle to a first epitope of the microorganism in a fluid by means of an antibody; using a magnetic field to separate the magnetic microparticle bound to the microorganism; binding a glucose molecule through a second antibody to the second epitope of the microorganism in question; and detecting the glucose in the sample to determine the presence and the concentration of the microorganism. The microparticles comprise microspheres of a superparamagnetic material coated with a polymer or protein, for example, albumin or avidin.

However, these methods have drawbacks which hinder their industrial application. These drawbacks include the following, among others:

1) The immobilization of the antibodies on the surface of the magnetic particles requires the presence in said surface of reactive groups, for example hydroxyl, amino or carboxyl groups. Once the antibodies have been bound to the surface by means of said reactive groups, there may be free groups which represent active sites to which other compounds present in the sample which can interfere in the antigen-antibody interaction, or in the composition of the developing reagents, or even the immobilized antibodies themselves the orientation of which to the external medium is altered, can also bind, making the interaction with the antigen and consequently the capture and recovery of the microorganism less likely.

2) The immunomagnetic particles collide with one another such that they can interact by means of weak bonds which can favor the formation of aggregates before the mixing with the sample, or after the mixing with the sample, an effect which depends on the concentration of the particle and on the contact time. This limits the possibility of reducing the limit of detection by increasing the amount of particle, and limits the useful life of the method based on using the particles.

3) The magnetic particles mixed with the complex sample can interact with some components which can favor the formation of aggregates, such that the interaction of the particle with the microorganism is less likely, and such that the efficiency of the magnetic retention is lower; consequently it makes the capture and recovery of the microorganism of interest less likely and the efficiency thereof decreases.

4) The quantitative recovery and handling of the immunomagnetic particles is not possible, fundamentally due to the previous drawback and mainly in large volumes of sample; consequently it is not possible to reduce the limit of detection by means of using large volumes of sample because there are variable losses of immunomagnetic particles and of complexes between the immunomagnetic particles and the microorganisms.

5) Some components present in the complex sample or in the solutions coming into contact with the particles in any or several of the separation steps can alter their coating, favoring the desorption of the blocking molecule, reactive groups being exposed in which other molecules which can be detrimental to the interaction of the microorganism with the immobilized antibody (capturing antibody), or said immobilized antibody, or the reading antibody, can be adsorbed.

6) The composition and concentration of different antigens which the microorganisms expose on their surface can change in response to changes in the environmental conditions (Albers U, Tiaden A, Spirig T, Al Alam D, Goyert S M, Gangloff S C, Hilbi H., "Expression of *Legionella pneumophila* paralogous lipid A biosynthesis genes under different growth conditions", Microbiology, 153 (Pt 11):3817-29, 2007), and consequently the sensitivity and reproducibility of the determination of the microorganism can depend on the origin of the sample and its environmental conditions.

7) The microorganisms of interest which are captured by means of the immunomagnetic particles can have endogenous enzymes which interfere with the reading of the complexes which they form with said particles, and which cannot be separated and removed without altering the structural integrity of the captured microorganism. These interferences are dependent on the concentration of the captured microorganism, such that for high concentrations of the microorganism, said interferences can cause an underestimation of the amount of the microorganism in a quantitative or semi-quantitative determination, or cause a false negative in a qualitative determination. In particular, the non-obligate anaerobic (aerobic, facultative anaerobic, aerotolerant and microaerophilic) microorganisms, such as, among others, *Escherichia coli, Staphylococcus, Legionella, Klebsiella, Bacillus, Salmonella, Campylobacter* or *Listeria*, have an endogenous enzyme, catalase, which competes for the hydrogen peroxide added as a substrate of the peroxidase enzyme, usually conjugated to the reading antibody.

In recent years there has been an increasing demand for information related to the determination of analytes of a varied nature in complex samples, and in increasingly more varied areas, in a rapid, simple and sensitive manner. To overcome the difficulties of conventional methods which prevent meeting this demand, a great effort in the analytical instrumentation field has been directed to obtaining devices the use of which does not require professional supervision, the handling of which is simple and the cost of which is lower, capable of providing analytical information in a rapid, selective, sensitive, reliable and decentralized manner.

This demand has favored the development of biosensors as analysis alternatives to conventional analytical instrumentation, for the purpose of separating the analyte from the complex matrix in which it is located and measuring its presence or its concentration.

The preparation of biosensors based on using magnetic particles has opened new perspectives of applications to any analysis with solid supports, especially in automatic systems.

There are several patent documents which relates to apparatuses working as biosensors and serving for the detection of microorganisms. Thus, document ES 2 220 227 A1 relates to a method and apparatus for the detection of substances or analytes from the analysis of one or several samples. The invention relates to a robotic apparatus which can be handled by remote control and to a method which allows analyzing multiple natural samples. Said invention benefits from the technology of proteins and DNA microarrays. The apparatus comprises a series of operative modules, in which the samples are handled, processed and analyzed, and a series of control modules, which supervise the operation of said operative modules. The method for analyzing the sample comprises reacting said sample with a biosensor, washing the excess of unreacted sample and detecting the sample retained in the biosensor. Document WO 93/25909 A1 relates to an apparatus for the detection of the presence of analytes of interest in a sample, particularly biosensors, as well as to the method for detecting the presence of an analyte, and document U.S. Pat. No. 7,220,596 B2 relates to the detection of antigens which can be captured and detected from samples such as foods, for example, in approximately 30 minutes by using an apparatus and method including the passage of the sample through a module containing antibodies bound to particles. The flow of the sample through the modified particles is 0.2 to 1.2 L/minute. The antigens are thus captured by the antibodies and then the detection of the antibodies is carried out by fluorescence, chemiluminescence, or spectrometry techniques.

Therefore, a method which can be carried out in situ, for example, by means of a kit, which allows detecting and semi-quantifying a certain pathogenic microorganism in a minimum time, such as 1 hour, for example, to be able to immediately take the necessary measurements, is still necessary.

Therefore, the present invention proposes simple kits and processes for the rapid and sensitive determination of the presence of microorganisms in a wide range of samples of an environmental or food origin, as well as in biological fluids, by means of immunomagnetic particles in suspension, which overcomes the previous drawbacks, allowing obtaining the result of the in situ analysis, in a time less than or equal to one hour, without limitation of volume of the sample, and for concentrations of the microorganism of interest of the order of 1 cell per milliliter, and enables the industrial application thereof.

OBJECT OF THE INVENTION

In one embodiment, the present invention provides a method for detecting and semi-quantifying in situ live microorganisms in a sample. In another embodiment, the present invention provides a method for quantifying live microorganisms from a sample in the laboratory. And in another embodiment, the present invention provides a method for detecting and quantifying live microorganisms by means of automated biosensor equipment.

It has surprisingly been found that it is possible to detect the presence or absence of a pathogenic bacterium, such as *Legionella, Salmonella* or *E. coli*, for example, in a biological sample by using methods which use a highly specific and highly sensitive biosensor. They are paramagnetic particles having on their surface antibodies specific for the microorganism to be detected and a blocking agent preventing the binding of contaminating molecules present in the biological sample.

The process of the present invention reduces the weak interactions which may occur between the particles as a result of the fact that said particles are protected throughout the analysis, by means of the constant blocking of their surface, obtained upon shifting the adsorption-desorption equilibrium of a blocking molecule towards the adsorbed molecule. Said blocking allows a dynamic inerting or coating, which conceals the reactive groups of the surface of the particle and prevents such interactions, such that the aggregation of particles is reduced, as well as their adhesion to the containing surfaces. At the same time, this is possible as a result of the fact that the concentration of the blocking agent, determining the amount of blocking molecule which can be adsorbed, and that of the buffers, determining the ionic strength to allow the blocking molecule to move closer to the surface of the particle, allow maintaining at all times the necessary amount of adsorbed blocking molecules and a suitable ionic strength so that said molecules can be rapidly replaced by others close to the surface of the support, and so that the reading molecules move closer to the captured microorganism; and furthermore, because combined chelating agents and surfactants are used to reduce the interferences of the sample due to the formation of insoluble complexes which are detrimental to the magnetic retention of the particles, and an inhibitor of the potentially interfering microbial activities which can compete with the reading molecule for the substrates used by said molecule for the development of the signal which is measured. Thus, all this enables a quantitative recovery of the particles which allows handling large volumes and improving the sensitivity of the method given that the absolute amount of cells of the microorganism of interest as well as the probability of collision, capture and retention of said microorganism increase.

The present invention also relates to a detection kit for the presence or absence of an antigen produced by a certain bacterium of the sample, containing the magnetic particles bound to specific antibodies directed against the corresponding antigens of the certain bacterium, as well as blocking molecules, a second labeled antibody and all the reagents necessary for carrying out the process.

Furthermore, the present invention also relates to automated biosensor equipment for the detection and/or semi-quantification and/or quantification of live microorganisms in the laboratory from a sample.

According to the present invention, microorganism is understood as any prokaryotic microscopic organism (including bacteria) or eukaryotic microscopic organism (including protozoa, algae, yeasts and fungi), not including viruses.

The bacteria fundamentally include those known as pathogenic bacteria, such as, for example, species of *Enterobacteriaceae, Vibrionaceae, Bacillus, Escherichia, Streptococcus, Pseudomonas, Salmonella, Legionella, Enterobacter*, etc.

A support is understood as a solid formed by a polymeric material which has, on its surface, a large number of chemical groups necessary for fixing molecules of interest.

Quantifying is understood as determining in an exact manner the concentration or amount of the microorganism of interest in the sample.

Semi-quantifying is understood as determining in an approximate manner the concentration of the microorganism of interest in the sample.

Detecting is understood as determining the presence-absence of the microorganism of interest in the sample.

In the present invention, a "sample" is considered as that which is suspected of containing the microorganism. The sample will generally be of an environmental or food origin, and in certain cases will be of biological fluids, such as, sputum, respiratory secretions or lung tissue, for example.

Antibody is understood as a molecule capable of recognizing and binding specifically to certain molecules exposed in the microorganism of interest, referred to as antigens. Said antibodies can be capturing or reading antibodies, and can be monoclonal or polyclonal.

Monoclonal antibody is understood as a homogeneous antibody derived from a single hybridoma clone, therefore all of them have identical antigen fixing sites.

Polyclonal antibody is understood as a heterogeneous set of antibodies targeted against different sites of the same antigen.

Reading antibody is understood as: an antibody interacting with its corresponding antigen exposed on the surface of the cell of the microorganism, conjugated with a molecule capable of producing a detectable signal, for example an enzyme catalyzing a reaction which produces a color or an absorbance change, or for example a molecule capable of producing a fluorescent emission.

Capturing antibody is understood as: an antibody which is immobilized on the surface of the support and interacts with its corresponding antigen exposed on the surface of the cell of the microorganism to form a support-microorganism complex. Oxidizing substrate refers to the chemical compound which gains electrons in a redox reaction.

Oxidizable substrate refers to the chemical compound which gives up electrons in a redox reaction. It is also referred to as reducing substrate.

Strong acid is that acid which, in aqueous solution, is completely dissociated into its constituent ions, providing hydrogen ions to the medium ($H^+$).

Strong base refers to the base which, in aqueous solution, is completely dissociated into its constituent ions, providing hydroxyl ions ($OH^-$).

Weak salt is understood as that salt which, in aqueous solution, is dissociated into its constituent ions only to a small extent, in contrast to a strong salt, which is dissociated by 100%.

Chelating agent refers to the compound which forms a soluble complex with the metal ions, referred to a chelate.

Surfactant refers to the agent which reduces the surface tension on the surface of contact between two phases.

Bacteriostatic agent is understood as that chemical substance which inhibits the growth and the reproduction of the microorganism without killing it.

Biocidal agent refers to that chemical substance which destroys the microorganism.

Thus, a first object of the present invention is formed by a process for detecting and/or semi-quantifying and/or quantifying microorganisms in a solution or suspension, which does not contain pre-cultured microorganisms, comprising the steps of:
a) mixing the sample suspected of containing the microorganism with i) a pH buffering suspension, comprising at least one type of paramagnetic particles which have, bound to their surface, an antibody specifically directed against the microorganism which is to be determined; and ii) at least one type of blocking agent molecule in excess on the surface of said magnetic particles not occupied by the antibody;
b) incubating the mixture for a determined time under conditions suitable for forming the microorganism-magnetic particle complexes;
c) applying a magnetic field for the separation and concentration of the microorganism-magnetic particle complexes formed; and subsequent evacuation of the supernatant;
d) resuspending the microorganism-magnetic particle complexes in a pH buffering solution, comprising at least one type of blocking molecule in excess and a second antibody labeled with a marker (an enzyme or a fluorophore);
e) incubating the mixture for a determined time to form the labeled antibody-microorganism-magnetic particle complexes;
f) applying a magnetic field for the separation and concentration of the labeled antibody-microorganism-magnetic particle complexes formed; and subsequent evacuation of the supernatant;
g) washing the particles to remove the excess of the second antibody, and subsequent evacuation of the supernatant;
h) resuspending the labeled antibody-microorganism-magnetic particle complexes formed in a liquid medium simultaneously containing the substrates necessary for the developing by means of the enzyme acting as a marker, a blocking agent at a concentration which allows maintaining the adsorption equilibrium shifted towards the bound blocking molecules, and an inhibitor specific for the intrinsic enzymes which compete for one or several of said substrates;
i) incubating the mixture for a determined time to develop the signal;
j) detecting and quantifying the signal resulting from the formation of the labeled antibody-microorganism-magnetic particle complexes, relating said signal to the presence and quantification of the microorganism sought.

In said process:
the sample is of environmental origin, food origin or obtained from biological fluids,
the microorganism is a prokaryotic microscopic organism, preferably bacteria and more preferably or eukaryotic microscopic organism, preferably protozoa, algae, yeasts and fungi, pathogenic bacteria, such as species of *Enterobacteriaceae, Vibrionaceae, Bacillus, Escherichia, Streptococcus, Pseudomonas, Salmonella, Legionella, Enterobacter*, etc., or an eukarytoic organism, preferably protozoa, algae, yeasts and fungi
the reading and/or capturing antibody for the microorganism of interest is monoclonal or polyclonal.
the magnetic particles are spherical and the diameter range is 0.5 μm to 2 μm, preferably 0.7 μm to 1.5 μm, and more preferably 0.8 μm to 1.0 μm, said particles being chemically functionalized especially with —$NH_2$, —COOH or —OH groups
during all the steps an excess of concentration of at least one type of blocking molecule is maintained, such that the adsorption-desorption equilibrium is shifted towards the adsorbed molecule, to prevent the non-specific adsorption on the magnetic particles, preventing false positives and false negatives.
the blocking molecule is a protein, preferably, bovine serum albumin, milk casein, coldwater fish skin gelatin, skin gelatin, skimmed milk, or a carbohydrate, preferably polydextrans.

the presence of a microorganism is detected visually in the solution or suspension, the production of color being indicative of the presence of the microorganism.

it allows using large volumes and/or successive loads of the same sample on the same supports constantly protected against unwanted adsorptions, increasing the sensitivity of the method.

it has a detection sensitivity of 1 cell/ml the result is obtained in a time less than or equal to one hour.

Another object of invention relates to the process in which the time in the immunocapture step is increased by increasing the sensitivity of the method due to the fact that the sustained protection of the surface of the particle prevents the increase of the non-specific adsorption throughout the analysis.

Another object of invention relates to the kit for carrying out the process described above, characterized in that it comprises: a reusable portable apparatus for manual use for in situ analysis and a set of reactive media or compositions for the performance of the analysis, all of this being arranged in a container incorporating a cooling plate. Said kit comprises a support with at least two cuvettes and a magnet, and a color chart for a correct interpretation of the results, the reactive media or compositions being:

a) composition for capturing the microorganism of interest, comprising a suspension of immunomagnetic particles (with the capturing antibody immobilized on the surface thereof by means of covalent bonding, and a blocking agent bound to the surface not occupied by the antibody, by means of non-covalent bonding), in a liquid medium containing in solution i) the same blocking agent, ii) a chelating agent, iii) a surfactant, iv) a biocidal agent, and v) a bacteriostatic agent, and having high ionic strength, corresponding to a phosphate buffer solution with a concentration between 90 and 500 mm, preferably between 100 and 200 mM, and more preferably 150 mM.

b) labeling composition for the microorganism of interest, comprising a reading antibody, conjugated with a reading molecule or a fluorescent substance, in a solution containing i) a blocking agent and ii) an inhibitor agent of the activity of enzymes present in the microorganism which can compete in the reading molecule, and having a medium ionic strength corresponding to a phosphate buffer solution with a concentration between 30 and 90 mm, preferably 50 mM and pH 6.0 phosphate citrate buffer.

c) reading composition for the microorganism of interest, comprising an oxidizable substrate necessary for the development of the reading reaction, in a solution containing a weak monosodium phosphate salt for reducing the autoxidation of said substrate.

d) reading composition for the microorganism of interest, comprising an oxidizing substrate, necessary for the development of the reading reaction, in a phosphate-citrate buffer solution, preferably with a pH of 6.0 and a concentration of 50 mM.

e) a stop composition for the reading reaction, comprising a strong acid or a strong base.

f) a composition for washing the immunomagnetic particles comprising a blocking agent, a surfactant and a bacteriostatic agent, with a low ionic strength corresponding to a phosphate buffer solution with a concentration between 5 and 30 mm, preferably sodium phosphate at pH 7.0 and a concentration between 20 and 30 mM, preferably 25 mM.

In said kit the blocking agent is a carbohydrate or protein, preferably protein, and more preferably a protein selected from the group of serum albumin, powdered milk casein, milk casein in solution, coldwater fish skin gelatin, pig skin gelatin, skimmed milk powder, polydextrans; etc the competition of the microbial enzymatic activity with the reading molecule is removed either by using an inhibitor specific for said activity, such as sodium azide or triazole, preferably triazole, or by using as oxidizing substrate for the reading enzyme, preferably peroxidase, a substituted peroxide, preferably urea peroxide, which is not recognized by the microbial enzymatic activity.

the oxidizing substrate is selected from hydrogen peroxide and urea peroxide, preferably 0.05% urea peroxide the oxidizable substrate is selected from 5-aminosalicylic acid, ortho-phenylenediamine, 2,2'-azino-bis(3-ethyl-benzothiazoline-6-sulfonic acid), preferably 0.1% 5-aminosalicylic acid the strong acid is selected from hydrochloric acid, nitric acid and sulfuric acid, preferably 5 M hydrochloric acid and 1 M sulfuric acid.

the strong base is selected from potassium hydroxide and sodium hydroxide, preferably 3 M sodium hydroxide.

the weak salt is dipotassium phosphate and disodium phosphate, preferably 0.1 M disodium phosphate.

the chelating agent is selected from 2,2'-bipyridyl, dimercaptopropanol, ethylenediaminetetraacetic acid (EDTA), ethylenedioxy-diethylene-dinitrilo-tetraacetic acid, ethylene-glycol-bis-(2-aminoethyl)-N,N,N',N'-tetraacetic acid (EGTA), nitrilotriacetic acid (NTA), ortho-phenanthroline, salicylic acid and triethanolamine (TEA), preferably EDTA.

the surfactant is selected from non-ionic detergents, preferably polyethoxylated alkyl phenols, polyethoxylated fatty alcohols, polyethoxylated fatty acids, alkanolamines or condensates, and more preferably sorbitan monolaurate (Tween 20).

the bacteriostatic agent is selected from p-nitrophenyl-dichloroacetamido propanediol (chloramphenicol), sulfanilamide, 2,4-diamino-5-(3,4,5-trimethoxybenzyl)pyrimidine (trimethoprim), preferably 2-(ethylmercuriomercapto)benzoic acid sodium salt (thimerosal).

the biocidal agent is selected from streptomycin, neomycin, gentamicin, kanamycin, and sodium azide, preferably sodium azide.

Another object of invention is formed by the kit described above, characterized in that:

a) in the composition for capturing the microorganism of interest, in the suspension, the immunomagnetic particles are spherical and have a mean diameter between 0.8 and 1.1 μm, the capturing antibody is a polyclonal or monoclonal anti-*Legionella* antibody, covalently bound to the surface of the particles, the blocking agent is bovine serum albumin (BSA) at a 10% concentration, the chelating agent is 0.1% ethylenediaminetetraacetic acid (EDTA), the surfactant is 1% sorbitan monolaurate, the biocidal agent is sodium azide at a concentration of 0.1%, and the bacteriostatic agent is thimerosal at a concentration of 0.01%, all this in a phosphate buffer solution with a concentration of 150 mM at pH 7.0. Said composition is added to the sample in a 1/10 ratio.

b) in the labeling composition for the microorganism of interest, the reading antibody is a peroxidase-conjugated anti-*Legionella* antibody, with i) the blocking agent being 0.1% bovine serum albumin (BSA) and ii) the inhibitor agent of the activity of enzymes present in the microorganism which can compete in the reading molecule being 0.01% triazole in a phosphate and citrate buffer solution with a concentration of 50 mM at pH 6.0, in the solution containing them.

c) in the reading composition for the microorganism of interest, the oxidizable substrate necessary for the development of the reading reaction is 0.1% 5-aminosalicylic acid and a weak disodium phosphate salt at a concentration of 0.1 M, at a pH between 7.5 and 8.0, to reduce the autoxidation of said substrate d) in the reading composition for the microorganism of interest, the oxidizing substrate, necessary for the development of the reading reaction, is hydrogen peroxide or urea peroxide, preferably 0.05% urea peroxide, in a phosphate-citrate buffer solution with a concentration of 50 mM at pH 6.0.

e) in the stop composition for the reading reaction, the strong acid is 5 M hydrochloric acid or 1 M sulfuric acid and the strong base is 3 M sodium hydroxide.

f) in the composition for washing the immunomagnetic particles the blocking agent is 0.1% bovine serum albumin, the surfactant is 0.02% sorbitan monolaurate and the bacteriostatic agent is 0.01% thimerosal in a phosphate buffer solution with a concentration of 25 mM at pH 7.0.

Another object of invention relates to the reusable manual analysis device for the detection or quantification of microorganisms in a solution or suspension following the process of the invention, comprising a support (1) containing a base (2) and two lateral inclined planes (3); a mobile shaft (4) supporting a magnet (5) and allowing its displacement with respect to the support; at least one fastener in the form of a clamp (7), and at least one cuvette (6) resting on the base and fixed in its position by the fastener in the form of a clamp (7) according to FIG. 2.

Another object of invention relates to the use of said manual device for the performance of the in situ analysis.

Another object of invention relates to the automated biosensor for carrying out the process described above, in an automated manner, characterized by consisting of an integrated system comprising i) cells for the capture and labeling reaction of the microorganism of interest.

ii) cells for reading the absorbance at the selected wavelength or the fluorescence at the selected emission length.

iii) an optical transducer which, in the case of *Legionella*, consists of a spectrophotometer or spectrofluorometer.

iv) a hydraulic circuit for handling the different liquids, v) a microprocessor for the sequential control of the analysis and the acquisition of the signal vi) a computer for processing data and its communication with the microprocessor.

vii) stirring devices.

viii) magnetic retention devices.

ix) thermostatic devices.

as depicted in FIG. 2. In said biosensor, each measurement cycle comprises the analysis of a blank and the analysis of a sample, the resulting absorbance value being the consequence of subtracting the signal of the blank from the signal of the sample.

Another object of invention relates to the use of the biosensor described above for the on-line monitoring of the concentration of a microorganism in water, based on using disposable aliquots of immunomagnetic particles for the capture of said microorganism. In a particular embodiment, said microorganisms are *Legionella*, and/or *Salmonella*, and/or *Escherichia coli*, and/or *Listeria*, and/or *Staphylococcus*, and/or *Streptococcus*, and/or *Brettanomyces*.

DESCRIPTION OF THE DRAWINGS

FIG. 4 presents the continuous recording of the absorbance readings at 550 nm over time, corresponding to a measurement cycle of the automated biosensor, which comprises the signal obtained for a blank (1) and a sample containing *Legionella pneumophila* (2) at a concentration of $2 \times 10^6$ cfu/l, said concentration determined in parallel by the culture method. The value resulting from subtracting the maximum absorbance value of the blank from the maximum absorbance value of the sample corresponds with the concentration of *Legionella* in the sample.

FIG. 3 presents the correlation obtained between the concentration of *Legionella* and the absorbance measured, both magnitudes expressed in logarithmic form, in sanitary water samples. The coefficient of correlation is high (r =+0.99), which implies that there is a high degree of consistency between the signal measured and the value of the concentration of the microorganism of interest in the sample.

FIG. 5 presents the values obtained for different sanitary water samples by means of the automated biosensor, and their parallelism with the corresponding values obtained by means of the culture method in a wide range of concentrations of between $10^3$ and $10^8$ cfu/l.

FIG. 6 presents the variation of the absorbance at 405 nm over time in the kinetic reading of two samples of one and the same concentration of the microorganism (*Escherichia coli*), with respect to a blank, without the microorganism (symbolized by a triangle). In one of the samples (symbolized by a square) said endogenous activity (catalase) has not been inhibited and in the other sample (symbolized by a circle) said activity has been inhibited. The drawing demonstrates that the sensitivity of the analysis (expressed as the variation of absorbance over time) considerably increases when the endogenous activity of the captured microorganism is inhibited (as is done in the present invention) because it competes with the reading molecule (peroxidase) for one of the substrates (hydrogen peroxide).

FIG. 8 shows the quantitative determination of *Legionella*. The table of FIG. 8 shows the correspondence for the concentration of *Legionella* between the values obtained by culture (1), and the values obtained by the process of the present invention, both in the quantitative implementation (2), and in the qualitative implementation (3), being able to observe that the present invention allows a reliable determination of the presence or amount of the microorganism of interest in the sample.

FIG. 9 shows the comparison of the protective effect against the non-specific adsorption of a static coating compared to a dynamic coating of the particle. The table of FIG. 9 shows the absorbance readings at 405 nm obtained upon assaying different concentrations of *Escherichia coli* for two different types of coating of the immunomagnetic particles. The static coating relates to the covalent bonding of a polymer on the surface of the particle (A), and the dynamic coating relates to the non-covalent bonding of a protein sustained over time by means of the forced shifting of the adsorption-desorption equilibrium of the protein towards the adsorbed molecule (B), the latter being the method carried out by the present invention. The discrimination of the concentrations of *Escherichia coli* in the samples and the proportionality of the readings obtained with said concentration are better with the dynamic coating (B) carried out by the present invention.

FIG. 10 shows the protective effect with respect to the non-specific adsorption of the pressure sustained over time of the blocking agent on the surface of the immunomagnetic particle. The table of FIG. 10 presents the dependence of the signal corresponding to the non-specific adsorption of the reading antibody on the surface of the anti-*E. coli* immunomagnetic particles, according to which the adsorption-desorption equilibrium of the blocking molecule remains (b) or not (a) shifted towards adsorption. The permanent blocking strategy based on maintaining the blocking pressure throughout the analysis allows significantly reducing the non-specific adsorption, a better sensitivity therefore being obtained because the signal difference between the blank and the sample is significantly greater.

FIG. 11 improves the determination by means of successive captures. The table of FIG. 11 presents a comparison between two particular embodiments of the present invention for measuring the concentration of *Legionella* in the same water sample. In one embodiment (A) the analysis comprises a single capture event, and in the other embodiment (B) the analysis comprises three successive capture events. The results demonstrate that by means of B, it is possible to increase the signal of the sample without increasing the signal of the blank, making the detection more sensitive, even though the time of the assay increases.

FIG. 12 shows the improvement of the determination by means of increasing the immunocapture time. The table of FIG. 12 presents a comparison between two particular embodiments of the present invention for measuring the concentration of *Legionella* in water. In one embodiment (a) the analysis comprises a 15-minute capture event, and in the other embodiment (b) the analysis comprises a 16-hour capture event (overnight). The results demonstrate that by means of b it is possible to increase the signal of the sample without increasing the signal of the blank, making the detection more sensitive, even though the time of the assay increases. In any case any of the two particular embodiments proposed by the present invention gives rise to reliable results.

FIG. 13 shows the discrimination between dead bacteria and live bacteria in the detection of *Legionella pneumophila*. The table of FIG. 13 presents the results obtained with the kit upon analyzing the samples with live *Legionella pneumophila* cells and dead *Legionella pneumophila* cells, at different concentrations. The figure shows how, as a result of the present invention, the dead cells which have been inactivated, are not detected for any concentration assayed, whereas the live cells are detected proportionally to their concentration.

FIG. 14 shows the comparison of quantitative results of the analysis of industrial water samples by means of PCR and by means of the present invention. The table of FIG. 14 shows the comparison of the analysis for the determination of the concentration of *Legionella* of two types of water samples (from cooling towers and from waste water), by means of plate culture, by means of polymerase chain reaction (PCR) and by means of the method of the present invention. The results show a high degree of consistency

DETAILED DESCRIPTION OF THE INVENTION

Figure 1:
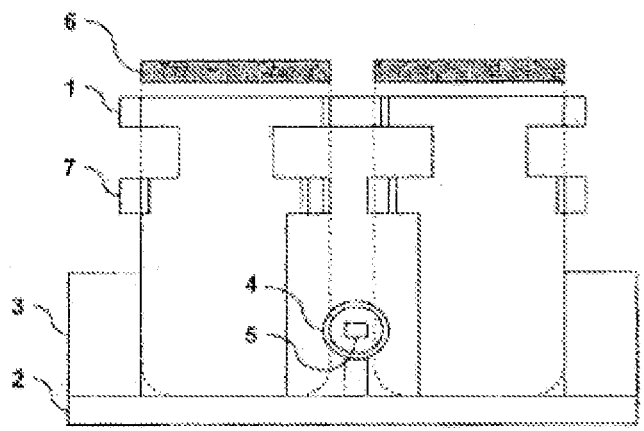
FIG. 1 shows a scheme of the device used in the invention for manually performing the analysis. As indicated in the drawing, this device comprises a support (1) containing a base (2) and two lateral inclined planes (3); a mobile shaft (4) supporting a magnet (5) and allowing its displacement with respect to the support; at least one fastener in the form of a clamp (7), and at least one cuvette (6) resting on the base and fixed in its position by the fastener in the form of a clamp (7).

The present invention provides a process for the detection and/or semi-quantification in situ of microorganisms in a sample, which comprises the steps of:
a) mixing the sample to be assayed with a suspension of superparamagnetic particles which have, bound to their surface, an antibody specifically directed against the microorganism which is to be determined; the active surface of the particle not occupied by antibody, being occupied by at least one blocking agent, adsorbed on said surface, in conditions of pH, ionic strength and concentration such that upon diluting the suspension with the sample, said conditions allow maintaining constant pressure of blocking agent molecules on the surface of said particles not occupied by the antibody; accordingly, the equilibrium between the bound and free blocking agent molecules is at all times shifted towards the bound blocking molecules.

Said suspension also contains at least one non-ionic detergent and at least one chelating agent to minimize the aggregation of the particles, without this affecting the antigen-antibody interaction.

b) incubating said mixture for a determined time under conditions suitable for allowing the formation of the microorganism-magnetic particle complexes;

c) applying a magnetic field for the separation and concentration of the microorganism-magnetic particle complexes formed; and evacuation of the supernatant;

d) resuspending the washed microorganism-magnetic particle complexes in a pH buffering solution, comprising at least one type of blocking molecule in excess and a second antibody labeled with a marker (an enzyme or a fluorophore);

e) incubating the mixture for a determined time to form the labeled antibody-microorganism-magnetic particle complexes;

f) applying a magnetic field for the separation and concentration of the labeled antibody-microorganism-magnetic particle complexes formed;

g) washing the particles to remove the excess of the second antibody, and evacuation of the supernatant;

h) resuspending the labeled antibody-microorganism-magnetic particle complexes formed in a liquid medium simultaneously containing the substrates necessary for the developing by means of the enzyme acting as a marker, a blocking agent at a concentration which allows maintaining the adsorption equilibrium shifted towards the bound blocking agent molecules, and an inhibitor specific for the intrinsic enzymes which compete for one or several of said substrates;

i) incubating the mixture for a determined time to develop the signal;

j) detecting and quantifying the signal resulting from the formation of the labeled antibody-microorganism-magnetic particle complexes, which is then related to the presence and quantification of the microorganism sought.

The present invention increases sensitivity by means of a technical creation which does not involve the necessary use of nanoparticles, but rather with microparticles it achieves sensitivities of 1 cell/ml (1000 cells/L), an order of magnitude greater than the best sensitivity achieved by means of using nanoparticles in the state of the art.

In the present invention, "sample" is considered as that which is suspected of containing the microorganism. The sample will generally be of an environmental or food origin, and in determined cases it will be from biological fluids, such as for example sputa, respiratory secretions or lung tissue.

The present invention uses which are generally prepared by means of the following steps:

a) preparing a suspension of magnetic particles with carboxyl groups on their surface at a concentration of 1%;

b) chemically treating the suspension of carboxylated magnetic particles so that the particles are activated, such that they are capable of covalently bonding to an antibody;

c) mixing the activated magnetic particles with the antibody to obtain immunomagnetic particles, i.e., with the antibody bound to their surface;

d) treating the immunomagnetic particles obtained in step c) to block the surface not occupied by the antibody;

e) treating the blocked immunomagnetic particles obtained in step d) to obtain a stable suspension.

The magnetic particles of the present invention are formed based on a polymer, generally polystyrene with 45-48% magnetic pigment, preferably with magnetite inclusions. They are of the spherical type and the range of the diameter is 0.5 μm to 2 μm, preferably 0.7 μm to 1.5 μm, and more preferably 0.8 μm to 1.0 μm. They are chemically functionalized, especially with —$NH_2$, —COOH or —OH groups, preferably with a 70-85 μeq/g of —COOH groups, on their surface. Other supports can be activated in the same manner, for example ferrofluids, which comprise magnetic particles of the order of 200-400 nm in diameter (nanoparticles), for example manufactured by Chemicell.

In an embodiment of the mentioned method, the treatment of step b) is carried out with ethylenedicarbodiimide (EDC) and N-hydroxysulfosuccinimide sodium salt (sulfo-NHS). Water-soluble EDC forms an active ester functional group with the carboxyl groups of the magnetic particle, using water-soluble sulfo-NHS. The sulfo-NHS esters are active hydrophilic groups which rapidly react with the amino groups of the antibodies.

The present invention provides a reusable analysis device for the detection or quantification of a microorganism of interest in an environmental or food sample, comprising a support (1) containing a base (2) and two lateral inclined planes (3); a mobile shaft (4) supporting a magnet (5) and allowing its displacement with respect to the support; at least one fastener in the form of a clamp (7), and at least one cuvette (6) resting on the base and fixed in its position by the fastener in the form of a clamp (7). A sample containing or potentially containing the microorganism of interest and in which all the detection or quantification steps takes place is applied on the cuvette, which comprises: (a) forming an assay mixture for selectively capturing and separating the microorganism of interest present or potentially present in the sample with a suspension of superparamagnetic particles sensitized with a recognition biomolecule which is selectively directed towards the microorganism to be detected or quantified, said assay mixture incorporating a capture medium the composition of which protects the particle from non-specific adsorption and from aggregation between particles; (b) incubating said assay mixture under conditions sufficient for allowing the binding of the recognition biomolecule to the microorganism of interest, a particle-microorganism complex thus being formed; (c) separating all the particles, including the particle-microorganism complexes, by means of applying a magnetic field; (d) washing all the particles in a washing medium which removes the components potentially interfering in the following steps of the analysis, and protects the particle from non-specific adsorption and from aggregation between particles; (e) forming an assay mixture by resuspending all the washed particles, comprising, (i) a reading biomolecule which is selectively directed towards the microorganism to be detected or quantified and (ii) a labeling medium the composition of which protects the particle from non-specific adsorption and from aggregation between particles; (d) incubating said assay mixture in conditions sufficient for allowing the binding of said reading biomolecule, a particle-microorganism-reading biomolecule complex thus being formed; (e) separating all the particles, including the particle-microorganism-reading biomolecule complexes, by means of applying a magnetic field; (f) washing all the particles in conditions sufficient for removing the reading biomolecule not bound to the particle-microorganism complexes, in a medium which protects the particle from non-specific adsorption and from aggregation between particles and (e) determining the presence or amount of said particle-microorganism-reading biomolecule complexes in a reading medium the composition of which removes the interferences due to the cell type object of the determination in the sample.

In the present invention, the antibody is not limited to a particular type and any type of antibody or fragment known in the state of the art which is specific for the microorganism to be determined can be used, including polyclonal antibodies, monoclonal antibodies, recombinant antibodies, etc. The antibodies can be specific for a microorganism species or even a genotype of a determined species, this case being useful for determining a specific contaminant, such as *E. coli* 0157:1-17 in foods for example. The antibodies can alternatively be reactive with the entire genus, the family or even the order of the microorganisms, this case being useful when it is to be determined if there is a general contamination, and not a contamination of a specific organism.

Methods for the production of antibodies, having both great or little specificity, are known by the person skilled in the art. Generally, the method of the present invention is used for detecting at least one microorganism in an aqueous solution or suspension. Thus, the method comprises mixing the solution or suspension with the microspheres coated with the antibodies. Examples of antibodies are those which are available on the market, such as for example, antibodies of Bionova Científica, S.L. Polyclonal antibodies are generally used in the method of the present invention because a polyclonal antibody is actually a population of different antibodies, such that said variation can dampen the variation of the expression of the antigens on the surface of a live bacterial cell. For example, in the case of the detection of *Legionella*, antibodies obtained in rabbit using a preparation of whole cells of the *Legionella pneumophila* strain, ATCC #33152, as an immunogen could be used in the corresponding case. The suitable amount of each antibody that is used with the microspheres can be easily determined by a person skilled in the art using routine experiments.

In one aspect of the invention, the treatment of step e) is carried out by means of mixing the blocked immunomagnetic particles with a solution containing an amount in excess of the blocking agent used in step d), a biocidal agent, a bacteriostatic agent, a surfactant and a chelating agent.

The blocking agents can be, between others, bovine serum albumin (BSA), bovine milk powder casein, bovine milk casein in solution, coldwater fish skin gelatin, pig skin gelatin, bovine skimmed milk powder, polydextrans, etc.

The biocidal agents can be, among others, streptomycin, neomycin, gentamicin, kanamycin, preferably sodium azide.

The bacteriostatic agents can be, among others, p-nitrophenyl-di-chloroacetamide propanediol (chloramphenicol), sulfanilamide, 2,4-diamino-5-(3,4,5-trimethoxybenzyl)pyrimidine (trimethoprim), preferably 2-(ethylmercuriomercapto) benzoic acid sodium salt (thimerosal).

The surfactants are essentially non-ionic detergents, such as, for example, polyethoxylated alkyl phenols, polyethoxylated fatty alcohols, polyethoxylated fatty acids, alkanolamines or condensates, etc., preferably sorbitan monolaurate (Tween 20).

The chelating agents can be, among others, 2,2'-bipyridyl, dimercaptopropanol, ethylenediaminetetraacetic acid (EDTA), ethylenedioxy-diethylene-dinitrilo-tetraacetic acid, ethylene-glycol-bis-(2-aminoethyl)-N,N,N',N'-tetraacetic acid (EGTA), nitrilotriacetic acid (NTA), ortho-phenanthroline, salicylic acid and triethanolamine (TEA), preferably EDTA.

In a particular embodiment, the blocking agent is bovine serum albumin (BSA), the bacteriostatic agent is thimerosal, the biocidal agent is sodium azide, the surfactant is sorbitan monolaurate, and the chelating agent is ethylenediaminetetraacetic acid (EDTA).

In an embodiment of the mentioned method, preservatives are added in step g), such as, for example, thimerosal for stabilizing the antibody conjugated with peroxidase. A weak disodium phosphate salt is used to delay the autoxidation of the co-substrate used in the reaction with peroxidase. Upon mixing it with the other co-substrate, dissolved in a phosphate-citrate buffer, the pH for which peroxidase activity is optimal is restored, such that the degree of autoxidation of the substrates has been insignificant, and the concentration thereof available for peroxidase is maximum, starting from a negligible level of autoxidation. It is also considered possible for the mixture of co-substrates with the weak salt to already be stable, such that in the end it is mixed with a phosphate-citrate buffer when it contacts with the peroxidase, thus assuring that the reaction occurs with a minimum initial level of autoxidation and at the optimal pH for peroxidase.

In an embodiment of the mentioned method, in the step h) inhibitors of the competitive endogenous enzymes of peroxidase are added, such as, for example, 3-amino-1,2,4-triazole, which selectively inactivates the microbial catalase that could compete with peroxidase for the development substrate (hydrogen peroxide), but does not inhibit peroxidase. Another possibility is to use a substituted peroxide which is not recognizable by catalase, but which is recognizable by peroxidase, for example urea peroxide.

By means of blocking the surface of the particle not occupied by the antibody, on one hand the adsorption on the particles of other molecules present in the sample, i.e., the non-specific adsorption that can hinder the capture of the microorganism of interest (favoring false negative) is prevented, and on the other hand the adsorption on the particles of the molecules which are used in the reading of the captured microorganisms (favoring false positive) is also prevented.

The adsorption of the antibody immobilized in the magnetic particle is also prevented because the blocking molecule prevents the immobilized antibody from becoming inclined on the surface and being able to be adsorbed without exposing its recognition region to the external medium. Aggregation of the particles to one another is reduced and their adherence to other surfaces is prevented, such as the walls of the vessel which contains them or in which they are handled.

The immunomagnetic particles thus obtained are stable in suspension for a long time period and are rapidly concentrated in suitable fractions by means of applying a magnetic field, being easily redispersed upon removing the magnetic field with gentle stirring.

The present invention achieves the quantitative handling of the particles by means of stabilizing the suspension of particles applied to the determination, and furthermore, throughout the determination process, from the contact with the sample until obtaining the analytical result, said conditions are sustained over time.

This stabilization means that at no time do the particles adhere to the containing surfaces, such that their number is not reduced during the analysis process, and that they cannot interact with other microorganisms or molecules different from the microorganism which is to be determined and with the determination of which they can interfere.

This feature requires blocking the surface of the particle that is not occupied by an antibody (the ligand used to capture the specific microorganism). The unblocked surface has a certain reactivity, such that other molecules or microorganisms present in the sample could interact and interfere in the interaction with the microorganism which is to be determined. There are methods for coating the particles or other supports by means of blocking agents such as polymers, for example dextran, by means of their covalent bonding to the surface of the particle. However, these techniques do not allow reproducible control of the degree of coating achieved, and it is even rather easy to coat part of the surface antibodies, such that the results can be quite variable or even compromise applying the particles.

Using blocking agents in specific steps of the determination in immunoassays to protect the surface in fixed supports, such as ELISA plates, is known. The blocking step is performed by incubating for a time the plate in a buffer containing a blocking agent. Part of the blocking molecules are adsorbed, and the unadsorbed molecules are subsequently washed, then proceeding with the development of the determination. In the composition of washing buffers, the presence of sodium chloride and phosphate salts is common. However, these compounds (especially sodium chloride) can in little time desorb blocking agents, such as certain proteins, the reactive surfaces of the particles being deprotected, which can favor non-specific interactions that may occur during the analysis.

It is obvious that using free supports, such as magnetic particles activated with antibodies, will allow an increase of collisions between the antibody and the antigen (present in the microorganism), such that part, not all, of these collisions will involve an antigen-antibody interaction and the most efficient capture of the microorganism at a given time. However, non-specific interactions of other molecules present in the sample with reactive groups of the surface of the particles can be favored in the same manner. These unwanted interactions could interfere in the desired antigen-antibody interaction.

On the other hand, both in the fixed supports (for example ELISA plates) and free supports (particles or spheres), the washing steps can also affect the degree of protection of the surfaces, either due to the effect of the composition of the washing buffers, or by simple dilution and subsequent shifting of the absorption equilibrium of the blocking agent, such that it is not true that said surfaces are protected in the same degree throughout the determination.

In free supports, such as the particles in suspension, the surfaces to be protected are those of said particles in suspension with free movement. This problem has been approached in the literature by means of applying synthesized polymers of the poly-alcohol type. These polymeric compounds are added at once as a step in the manufacture of the particles, and they are bound directly to the surface. The adsorption of the blocking agent molecules is favored at all times in the present invention. To that end, the adsorption-desorption equilibrium remains at all times shifted towards the adsorption of the blocking molecule. Preferably, this blocking agent is a protein.

Since the control of the reactions involved in the deposition and covalent bonding of synthetic polymers on the surface of the support is not reproducible, the degree of coating achieved is quite variable, and in fact it is very common for part, and not always the same part, of the antibodies immobilized on the surface of the particle to also be coated, losing their capacity to interact with the antigen.

This is the case because the chemistry used always affects some of the very diverse reactive groups which antibodies have, being inevitable for the polymers to interact with some of them, or because the polymer is completely or partially deposited on some antibodies, causing a steric hindrance a the interaction with the antigen.

It is therefore necessary to achieve an inerting of the particle which is reproducible and which does not depend on the changing conditions of the environment for the process of determining the microorganism.

The present invention solves the problem and achieves the inerting by means of a process based on maintaining constant pressure of the blocking agent throughout the determination process, both in the incubations, washings and separations. The number of blocking agent molecules abandoning the surface at a given time is thus always compensated by an equivalent number of blocking agent molecules which occupy their place. This involves considering the following aspects:

a) the addition of the blocking agent as a final step of the process for manufacturing the immunoreagent (the particle with the immobilized antibodies), at such a concentration that upon adding the envisaged amount of suspension to a sample for performing an analysis, the dilution obtained allows maintaining an optimal concentration of the blocking agent;

b) the introduction of the blocking agent in all the solutions involved in the analysis, such that the optimal concentration of blocking agent is maintained for all the steps of the analysis;

c) the interaction of the blocking agent with the surface does not require covalent bonding, but rather it is based on weak, multi-point interactions, establishing an adsorption to the support, the equilibrium of which is shifted towards the binding with the support. It is a "dynamic" protection system of the activated particles with the antibodies, which avoids the need for a synthesis polymer and the introduction of covalent bonds.

The present invention thus provides a robust determination process, characterized in that the following effects are sustained over time:

1) the surface of the particle is not deprotected, and non-specific adsorptions are accordingly minimized;

2) the antibodies cannot move close to the support in their rolling movement around their anchoring point, and be adsorbed in the actual support, and accordingly there is no loss of biological activity;

3) the handling of the particles, the particles with the antibodies, the particles with the immunocomplexes, and the particles with the labeled immunocomplexes (for measuring), is at all times quantitative, eliminating its influence on the variability of the measurement, unlike what occurs with an ELISA or even with conventional magnetic particles, regardless of their composition.

An aspect of great interest is that due to the sustained protection of the surface of the particle against non-specific adsorption, it is possible to increase the amount of reading antibody under conditions of low ionic strength in order to increase the probability of collision between the microorganism captured on the particles and said reading antibody. This is possible because under conditions of low ionic strength the electrostatic repulsions between the reading antibody and the antigen exposed on the surface of the captured microorganism are reduced. Accordingly, the reading antibody can move even closer to the antigen, and a larger number of favorable collisions can occur in less time. At the same time, the interaction of the blocking molecule with the surface of the particle not occupied by the capturing antibody is favored. Therefore, an efficient protection of the surface of the particle against non-specific adsorption and an efficient antigen-antibody interaction occur at the same time. Accordingly, the sensitivity of the determination increases, maintaining a high signal/noise ratio.

Another aspect of the greatest interest is that the quantitative handling of the particles in this controlled and constant environment allows handling large volumes of sample and increasing sensitivity of the determination. It is possible to increase sensitivity by means of increasing the volume of sample, which is a very important limitation in other immunoassay techniques, such as ELISA technique.

In the present invention, it is also possible to increase the sensitivity by means of applying several loads (equivalent amounts by volume) of the same sample on the same particles. When the capture is performed on a determined load of sample, it is known in the initial moments that there is a very large number of cells of the microorganism, such that the encounter between particle and microorganism is very favorable, the capture thereof occurring by means of the antigen-antibody interaction.

Generally, as time elapses, the "empty" particle population (without bound microorganism) reduces in favor of the particle population which has captured the microorganism; the free microorganisms also decrease in number in the sample, and the particles become increasingly less efficient in the capture because they already have bound cells of the microorganism, making the entrance of another cell difficult, and because there is less free microorganism in the sample and the favorable collisions are less probable. For this reason, the incubation times in the immunoassays are usually long, between 30 minutes and three hours, for example.

In a particular embodiment, the present invention provides a process for improving the capture efficiency without altering the incubation time, or even reducing it, which consists of dividing the sample into equivalent and homogenous aliquots (loads), and subjecting a first load to contact with the magnetic particles activated with the antibody for a time less than t1; then retaining the particles, removing the sample and replacing it with a fresh load of sample, such that the same particles (depleted in the sense that now they are capable of capturing fewer cells because part of their surface is already occupied) are in an environment again with the same concentration of free bacterium, favoring new interactions, for a time t2 which can be greater than t1; and so on for as many loads required. Thus, $T=t1+t2+\ldots+tn$, where T is the total time of immunocapture (FIG. 11).

In another particular embodiment, the present invention provides a process for increasing the sensitivity of the determination of the microorganism of interest by means of increasing the time of the single immunocapture step, because the non-specific adsorption is not increased due to the sustained protection of the surface of the particle (FIG. 13).

Thus, the present invention provides processes for increasing sensitivity in a very significant manner because it allows using larger volumes of sample, and/or successive loads of one and the same concentration of microorganism, using supports which are constantly protected against unwanted adsorptions throughout the process.

The present invention provides a kit for the determination of microorganisms. The scope of said determination can be semiquantitative or quantitative; semiquantitative determination is understood as one in which the result is an estimation of the order of magnitude of the concentration of the microorganism of interest in the sample. The kit allows the selective capture of the microorganism of interest in water or food samples, its concentration and separation from the remaining components of the sample, and its colorimetric detection, in a simple and rapid manner, in situ determination being possible. The kit uses superparamagnetic particles with antibodies directed against the microorganism of interest, immobilized on their surface, which in the supplied reaction media bind specifically to the microorganism of interest that is present or potentially present in the sample. An easy to handle portable apparatus allows moving a magnet closer to and away from the reaction cuvette. This makes the retention and resuspension of the particles during the analysis for the immunomagnetic capture, separation and concentration of the microorganism of interest possible. Finally, the reactive medium in the cuvette develops a color which is compared with a color chart to visually determine the presence of the microorganism of interest and to estimate its order of magnitude in an approximate time of 60 minutes between sampling and obtaining the result.

In a particular embodiment, the kit comprises a portable apparatus for manual use for in situ analysis and a set of compositions or reactive media for performing the analysis, all arranged in a container incorporating a cooling plate. All the steps of the analysis take place in said apparatus, comprising a support with two cuvettes and a magnet, and a color chart for a correct interpretation of the results. Said compositions or reactive media are the following:

a) composition for capturing the microorganism of interest, comprising a suspension of immunomagnetic particles (with the capturing antibody immobilized on the surface thereof by means of covalent bonding, and a blocking agent bound to the surface not occupied by the antibody, by means of non-covalent bonding), in a liquid medium containing in solution the same blocking agent, a chelating agent, a surfactant, a biocidal agent, and a bacteriostatic agent. Said composition has a high ionic strength corresponding to a sodium phosphate buffer with a concentration of 150 mM.

b) labeling composition for the microorganism of interest, comprising a reading antibody, conjugated with a reading molecule, for example peroxidase, or a fluorescent substance, in a solution containing a blocking agent and an inhibitor agent of the activity of enzymes present in the microorganism which can compete in the reading molecule. Said composition has a medium ionic strength corresponding to a 50 mM phosphate-citrate buffer and pH 6.0.

c) reading composition of the microorganism of interest, comprising a oxidizable substrate necessary for the development of the reading reaction, in a solution containing a weak disodium phosphate salt for reducing the autoxidation of said substrate.

d) reading composition of the microorganism of interest, comprising an oxidizing substrate, necessary for the development of the reading reaction, in a phosphate-citrate buffer solution at pH 6.0 and concentration 50 mM.

e) a stop composition for the reading reaction, comprising a strong acid or a strong base, at a concentration between 1 M and 5 M, preferably 3 M.

f) a composition for washing the immunomagnetic particles comprising a blocking agent, a surfactant and a bacteriostatic agent, with a low ionic strength corresponding to a sodium phosphate buffer solution at pH 7.0 and concentration 25 mM.

In a particular embodiment, the present invention provides automated biosensor equipment for the on-line monitoring of the concentration of *Legionella* in water based on the use of disposable aliquots of anti-*Legionella* immunomagnetic particles.

The configuration of the biosensor for the continuous monitoring of the concentration of *Legionella* in water is described below. The biosensor is an integrated system including:

i) cells for the capture and labeling reaction of the microorganism of interest, in this example *Legionella*.

ii) cells for reading the absorbance at the selected wavelength or the fluorescence at the selected emission length.

iii) an optical transducer (a spectrophotometer or spectrofluorometer in the case of *Legionella*).

iv) a hydraulic circuit for handling the different liquids, v) a microprocessor for the sequential control of the analysis and the acquisition of the signal vi) a computer for processing data and its communication with the microprocessor.

vii) stirring devices, viii) magnetic retention devices.
ix) thermostatic devices.

Figure 2:
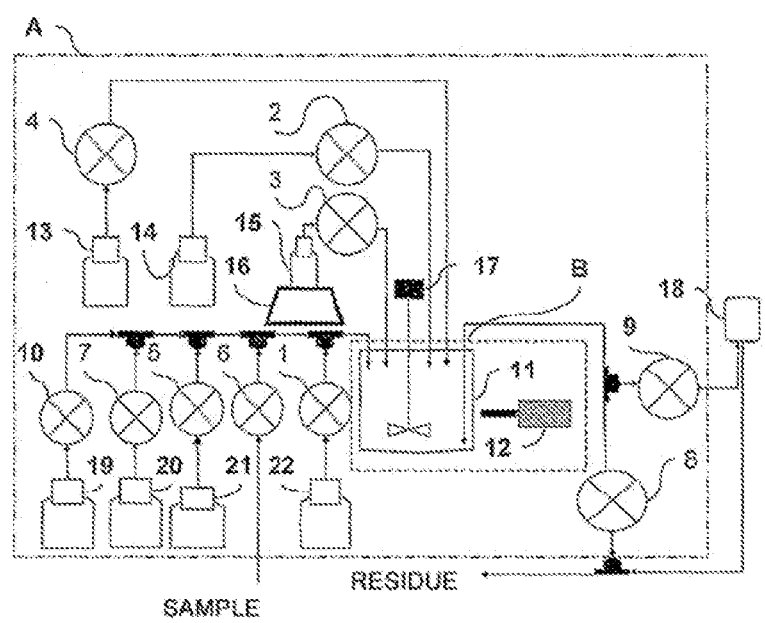
FIG. 2 shows a scheme of the automated biosensor used in the invention for automatically performing the analysis. As indicated in the drawing, the biosensor comprises two compartments, A and B, B being contained in A. Compartment A comprises an assembly of peristaltic pumps and reservoirs. A standard substance or blank is transferred from a reservoir (22) to the reaction cell (11) by means of a peristaltic pump (1); the sample is transferred from the sampling point by means of a peristaltic pump (6) to the reaction cell (11); a composition containing the suspension of immunomagnetic particles is homogenized by means of a stirring device (16) and transferred from the corresponding reservoir (15) by means of a peristaltic pump (3) to the reaction cell (11); a stirring device (17) allows homogenizing the mixtures in the reaction cell (11); a magnetic retention device (12) allows activating or deactivating a magnetic field on the reaction cell (11); a peristaltic pump (8) allows evacuating the content of the reaction cell (11) to residue; a composition containing an antibody directed against the microorganism of interest, referred to as reading antibody, is transferred from its reservoir (14) to the reaction cell (11) by means of a peristaltic pump (2); a composition which allows washing the immunomagnetic particles is transferred from its reservoir (20) to the reaction cell (11) by means of a peristaltic pump (7); a composition containing the substrates of the peroxidase enzyme (reading composition) is transferred from its reservoir (13) to the reaction cell (11) by means of a peristaltic pump (4); a composition containing a stop reagent is transferred from its reservoir (21) to the reaction cell (11) by means of a peristaltic pump (5); a peristaltic pump (18) transfers its content from the reaction cell (11) to the reading cell (18) by means of a peristaltic pump (9), passing therethrough a stream which is evacuated to residue; a cleaning composition for the hydraulic circuit is transferred from its reservoir (19) to the reaction cell (11) by means of a peristaltic pump (10); the reading cell coupled in a transducer (18) is loca (11) and the magnetic retention device (12) are in compartment ted outside compartment A, the reaction cell B, in turn inside A, and all the other elements are in compartment A. Compartment A is thermostated at a temperature of 4-8° C., and the compartment B is thermostated at a temperature of 24-26° C. The reading cell (18) is at room temperature.

FIG. 2 shows the configuration of the biosensor. The capture and labeling of the microorganism of interest, on one hand, and the reading of signal obtained, on the other, take place in different cells. The hydraulic circuit is made up of peristaltic pumps which allow handling the liquids. A magnetic retention device allows handling the immunomagnetic particles in a reaction cell, in which the capture and labeling of the microorganism of interest takes place, and the reading of the signal takes place under flow in another different cell integrated in the transducer component. The reaction cell and the magnetic retention device are located in a thermostated compartment (B) to maintain the temperature favorable for the antigen-antibody interaction and the optimal temperature for the activity of the reading molecule. Said compartment is in turn inside another larger thermostated compartment (A) at a temperature favorable for the conservation of the reagents and solutions involved in the analysis.

In each measurement cycle, the capture, separation and concentration of the microorganism of interest present in the sample, and subsequently its reading, take place. The measurement of a blank comprising a solution free of the microorganism of interest takes place in a first step of the cycle, and the measurement of the microorganism of interest in the sample takes place in a second step.

Figure 3:
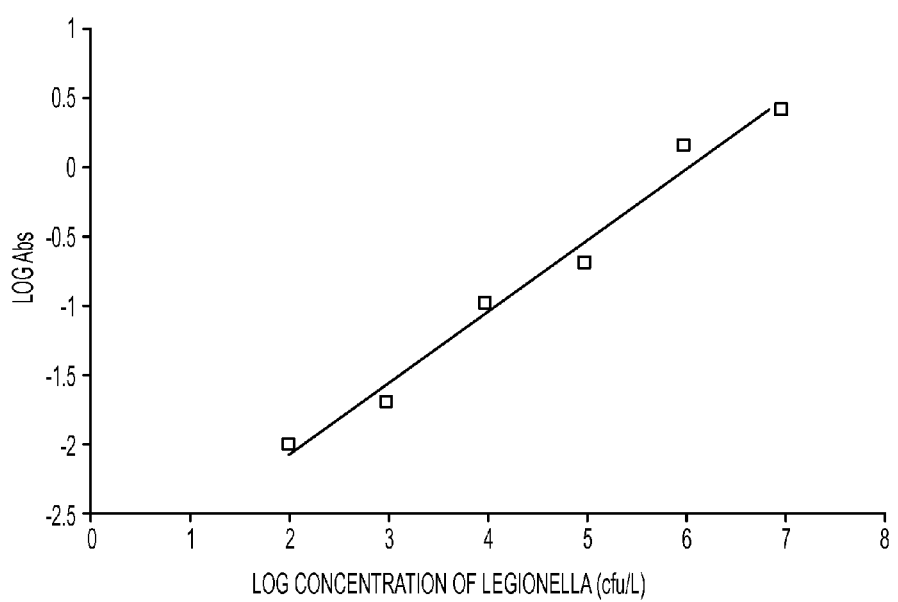
FIG. 3 shows the correlation between the absorbance and the concentration of *Legionella* in sanitary water.

The apparatus records the reading of the blank and the reading of the sample FIG. 2), and calculates the difference between both, the value of which is correlated with the concentration of the microorganism in the sample (FIG. 3). To that end, using the automated device depicted in FIG. 2 (the different integrating parts of which are identified between brackets below), predetermined amounts of the following compositions in the following order are added in each case, both for the blank and for the sample: (a) a predetermined volume of sample is transferred from the sampling point by means of a peristaltic pump (6) to the reaction cell (11), located in a thermostated compartment (B); (b) an aliquot of a composition containing the suspension of immunomagnetic particles, after homogenization by means of a stirring device (16), is transferred from the corresponding reservoir (15) by means of a peristaltic pump (3) to the reaction cell (11); c) the mixture of the sample and the immunomagnetic particles is homogenized by means of a stirring device (17), at regular time intervals, for a predetermined period, so that the microorganism of interest can be captured by the immunomagnetic particles by means of the antigen-antibody interaction, forming particle-microorganism complexes; d) application of a magnetic field by means of the activation of the magnetic retention device (12), such that the immunomagnetic particles, both free and those which have formed complexes with the microorganism of interest, are retained in an area of the reaction cell (11); e) evacuation of the supernatant liquid to residue by means of a peristaltic pump (8); f) removal of the magnetic field applied by means of deactivating the magnetic retention device (12); g) a predetermined volume of a composition containing an antibody directed against the microorganism of interest, referred to as reading antibody because it is conjugated with a reading molecule, for example peroxidase, is transferred from its reservoir (14) to the reaction cell (11), by means of a peristaltic pump (2); h) the mixture of the immunomagnetic particles with the previous composition in the reaction cell (11) is homogenized by means of stirring with a stirring device (17), at regular time intervals, for a predetermined period, so that said reading antibody can bind to the microorganism captured on the immunomagnetic particles; i) application of a magnetic field by means of activating the magnetic retention device (12), such that the immunomagnetic particles, both free and those which have formed complexes with the microorganism of interest and the reading antibody, are retained in an area of the reaction cell (11); j) evacuation of the supernatant liquid to residue by means of a peristaltic pump (8); k) removal of the magnetic field applied by means of deactivating the magnetic retention device (12); l) a predetermined volume of a composition which allows washing the immunomagnetic particles is transferred from its reservoir (20) to the reaction cell (11) by means of a peristaltic pump (7); ll) the mixture of the immunomagnetic particles and the washing composition is homogenized with a stirring device (17); m) application of a magnetic field by means of activating the magnetic retention device (12), such that the washed immunomagnetic particles are retained in an area of the reaction cell (11); n) the supernatant liquid is evacuated from the reaction cell (11) to residue by means of a peristaltic pump (8); o) removal of the magnetic field applied by means of deactivating the magnetic retention device (12); p) a predetermined volume of a composition containing the substrates of the peroxidase enzyme (reading composition) is transferred from its reservoir (13) to the reaction cell (11) by means of a peristaltic pump (4); q) the mixture of the immunomagnetic particles and the previous composition is homogenized with a stirring device (17), for a determined period, in which the peroxidase catalyzes the obtaining of soluble colored product; r) a predetermined volume of a stop reagent is transferred from its reservoir (21) to the reaction cell (11) by means of a peristaltic pump (5) to stop the reaction caused by the reading molecule; rr) application of a magnetic field by means of the activation of the magnetic retention device (12), such that the immunomagnetic particles are retained in an area of the reaction cell (11); s) the supernatant is transferred from the reaction cell (11) to residue, making it pass under flow through the reading cell (18) by means of a peristaltic pump (9); said cell housed in an optical transducer which allows recording the absorbance readings during the passage of said supernatant to determine the presence or amount of the microorganism of interest.

The blank is analyzed in the same manner as the sample and prior to the latter; to that end, the blank is transferred from its reservoir (22) to the reaction cell (11) by means of the peristaltic pump (1).

Finally, the reading obtained for the blank is compared with the reading obtained for the sample. Said comparison consists of subtracting the maximum absorbance value recorded from the blank from the maximum absorbance value recorded for the sample.

Once the measurement cycle has ended, the hydraulic circuit of the biosensor is washed, passing a cleaning solution from its reservoir (19) to the reaction cell (11) by means of a peristaltic pump (10). The cleaning solution contained in the reaction cell (11) is stirred by means of a stirring device (17) for a determined time and is passed through the reading cell (18) to residue by means of a peristaltic pump (9).

Some examples are described below, although many others are comprised within the scope of the invention in a manner that is evident to the person skilled in the art.

EXAMPLES

Example 1

Detection of *Legionella* in a Sanitary Water Sample

Superparamagnetic particles of polystyrene (mean diameter of 0.9 µm, 45.7% magnetic pigment-Estapor Merck France) which have carboxyl groups on their surface are used. An anti-*Legionella* polyclonal antibody is immobilized on these particles. The immunomagnetic particles were incubated in a 25 mM phosphate buffer solution at pH 7.0 with 1% BSA for 12 hours, under gentle stirring. The resulting immunomagnetic particles were suspended in a 1/40 ratio in a 150 mM phosphate buffer solution containing 10% BSA, 1.0% Tween 20, 0.01% thimerosal, and 0.1% sodium azide. The final suspension of immunomagnetic particles is deposited in a portable apparatus for in situ analysis, similar to that which is shown in FIG. 1 and described above.

With the magnet away from the cuvette, a volume of 1.0 ml of the suspension of immunomagnetic particles is deposited inside the cuvette, and then a volume of 10.0 ml of water sample directly from of a cooling tower is added on the immunomagnetic particles, forming a mixture which is homogenized by means of gentle stirring of the apparatus and it is incubated at room temperature for 15 minutes. After this incubation time has elapsed, the magnet moves closer until contacting with the outer wall of the cuvette and the immunomagnetic particles are attracted and retained in the area adjacent to the magnet, in the inner wall of the cuvette. The supernatant is evacuated from the cuvette, without entraining the immunomagnetic particles retained by the magnetic field.

Then, the immunomagnetic particles retained in the cuvette are resuspended in a volume of 1.0 ml of a 50 mM phosphate-citrate buffer solution at pH 5.0, containing 0.1% BSA, 0.01% thimerosal, and 4.0 µg/ml of an anti-*Legionella* Spp. polyclonal antibody conjugated with peroxidase. This mixture is homogenized by means of gentle stirring of the apparatus, and incubated at room temperature for 10 minutes. After the incubation, the magnet moves closer until contacting with the outer wall of the cuvette and the immunomagnetic particles are attracted and retained in the area adjacent to the magnet, in the inner wall of the cuvette. The supernatant is evacuated from the cuvette, without entraining the immunomagnetic particles retained by the magnetic field.

The immunomagnetic particles are washed by means of their resuspension, with the magnet away from the cuvette, in a volume of 4.0 ml of a 25 mM phosphate buffer solution at pH 7.0 containing 1% BSA, 0.1% Tween 20, and 0.1% thimerosal, and then retaining said washed immunomagnetic particles, again by means of moving the magnet closer and contacting it with the cuvette to evacuate the supernatant. This washing step is performed two more times.

Following the last washing, the magnetic field is removed, i.e., the magnet is moved away from the cuvette; the immunomagnetic particles are resuspended in a volume of 1.0 ml of a 50 mM phosphate-citrate buffer solution at pH 5.0, containing 0.5% urea peroxide and 0.1% aminosalicylic acid. This mixture is homogenized by means of gentle stirring of the apparatus, and is incubated at room temperature for 2 minutes. During this time, the peroxidase conjugated to the anti-*Legionella* polyclonal antibody, in turn bound to the complexes formed by the immunomagnetic particles and the captured *Legionella* cells, catalyze the oxidation of the aminosalicylic acid by the urea peroxide. This reaction gives rise to a coloring of the mixture in the apparatus.

After the incubation has elapsed, 0.15 ml of a 3 M sodium hydroxide (NaOH) solution is added to the mixture to stop the reaction catalyzed by the peroxidase. After 1 minute has elapsed, after the incubation, the magnet moves closer until contacting with the outer wall of the cuvette and the immunomagnetic particles are attracted and retained in the area adjacent to the magnet, in the inner wall of the cuvette.

Figures 6, 7:
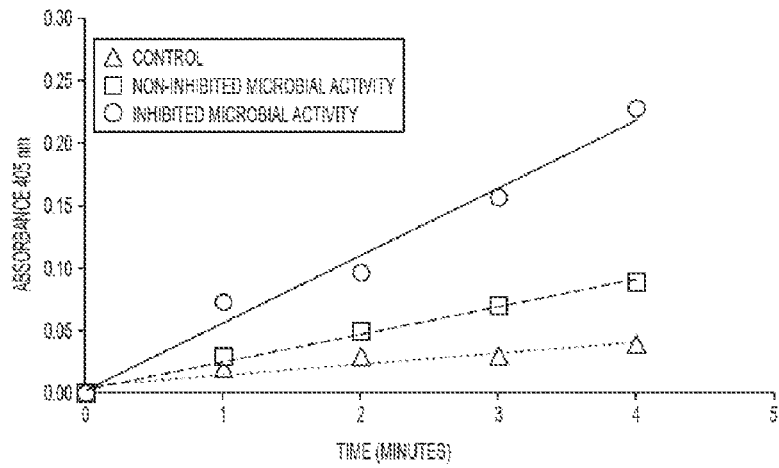
FIG. 6 shows the effect of the endogenous activity of the captured microorganism on the sensitivity of its determination.
FIG. 7 shows the semiquantitative determination of *Legionella* Spp. According to the table of FIG. 7, the order of magnitude of the concentration of *Legionella* in the sample, expressed as colony forming units per liter (cfu/l), can be estimated according to the color developed by the kit. The different ranges of absorbance correspond with different intensities of the color produced, visually distinguishable without the need for optical reading.

The production of a coloring is interpreted as a positive result in the detection of *Legionella*, and the absence of coloring as a negative result. The intensity of the final coloring obtained allows visually estimating the order of magnitude of the concentration of *Legionella* (expressed as colony forming units per liter, cfu/l) (FIG. 7).

The supernatant can be evacuated to perform the reading of its absorbance at a wavelength of 550 nm. With respect to the absorbance reading of a blank, said absorbance correlates to the concentration of *Legionella* in the sample (FIG. 3).

This absorbance is proportional to the amount of *Legionella* captured by the immunomagnetic particles, which in turn is proportional to the amount of *Legionella* present in the sample.

The results obtained for samples of different concentrations of *Legionella*, with 15 replicas per sample are consistent between the culture method and the method provided in the present invention, both qualitatively and quantitatively (FIG. 8).

These results confirm the validity of the processes provided by the present invention for the detection and/or semi-quantification or quantification of live microorganisms from a sample.

Example 2

Quantitative Analysis of Industrial Water (Cooling Towers and Waste Water)

According to the process provided in the present invention in Example 1, two types of water samples were analyzed: samples from cooling towers and samples from waste water. For each type of sample, concentration of *Legionella* is determined by means of the plate culture, by means of polymerase chain reaction (PCR) and the analysis is performed by the method of the present invention, obtaining the reading of the absorbance at 550 nm. The volume of each sample assayed with the method of the invention is 10.0 ml and the samples were not pretreated.

As can be observed in FIG. 14, the obtained results indicate a high degree of consistency between the concentration of *Legionella* in the sample and the absorbance reading at 550 nm for the two assayed types of sample.

Accordingly, the method provided by the present invention allows obtaining an reliable estimation of the concentration of *Legionella* in different types of water, with significant advantages with respect to the other techniques used, and particularly, the time of obtaining the result, which is less than one hour, the possibility of performing the in situ analysis, and without the need of professional supervision in a controlled laboratory environment.

Example 3

Quantification of *Legionella* by Means of an Automated Biosensor

This example presents the results obtained for sanitary water samples with different concentrations of *Legionella*, with 7 replicas per sample, by means of using the automated biosensor equipment described (FIG. 2) for the on-line monitoring of the concentration of *Legionella* in water based on using disposable aliquots of anti-*Legionella* immunomagnetic particles.

Figure 4:
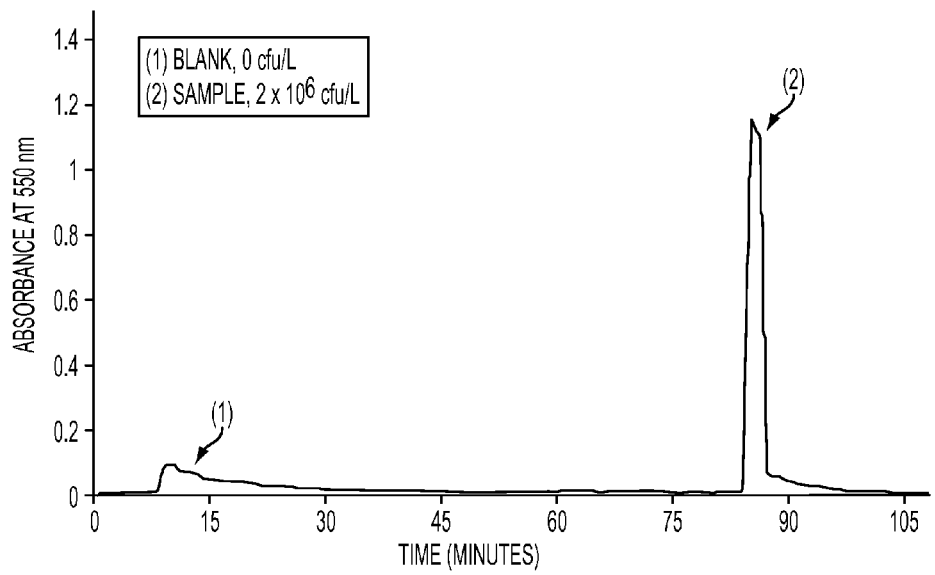
FIG. 4 shows a recording obtained in the automated biosensor of the signal of a blank (without *Legionella*) and the signal of a sample (with *Legionella*).

Each measurement cycle comprises the analysis of a blank and the analysis of a sample, and the corresponding signals are recorded by the automated biosensor (FIG. 4). The absorbance value resulting from subtracting the signal of the blank from the signal of the sample has a high correlation with the concentration of *Legionella* in the sanitary water sample (coefficient of correlation r=+0.99) (FIG. 3).

Figure 5:
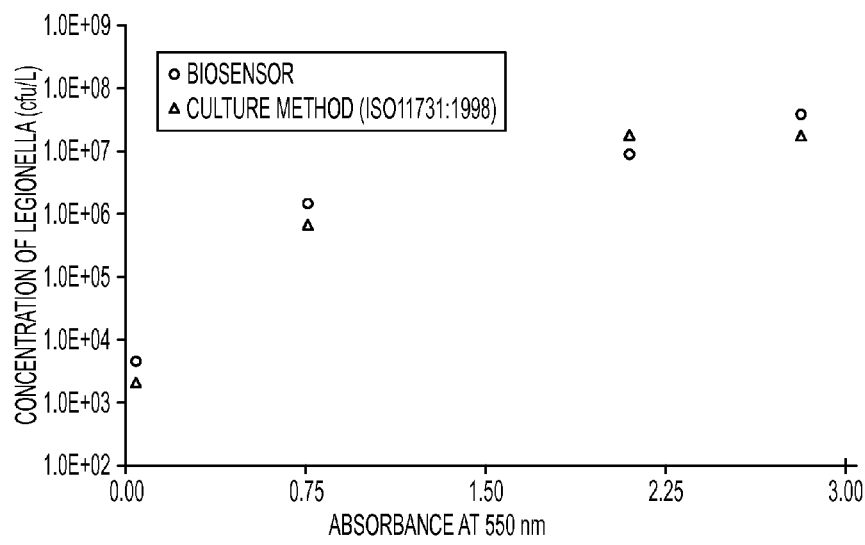
FIG. 5 shows the results obtained with the automated biosensor for sanitary water samples and their correspondence with the culture method.

As shown in FIG. 5, the results obtained by means of the culture method and the method provided in the present invention for the automated biosensor are comparable. The measurement cycle has a duration of 1 hour per analyzed sample.

This suggests that the biosensor can be used for the monitoring and surveillance of the concentration of *Legionella* in water, mainly in risk installations, and even for applying in a suitable and proportional manner the dosage of biocides or other corrective measures. Particularly, the biosensor can be used to prevent the risk installations from reaching infective concentrations of *Legionella* sustained over time, reducing the probability of the associated risk. These concentrations for cooling towers and similar devices have been reported, establishing as such those concentrations which reach or exceed $10^4$-$10^5$ cfu/L (World Health Organization, "*Legionella* and the prevention of legionellosis", 2007). These concentrations have been determined by culture in a time of 12-15 days. Taking into account that the concentration of *Legionella* can be multiplied by a factor of 10 or 100 in a few minutes in a risk installation (Bentham & Broadbent, "The Influence of the Sessile Population in the *Legionella* Colonization of Cooling Towers in: *Legionella*—Current Status and Emerging Perspectives, Eds. Barbaree, J. M., Breiman, R. F. and Dufour, A. P., ASM Press. Washington, D.C., 1993), the culture method cannot be used for the purpose of prevention but rather only as a verification tool.

However, the biosensor presented by the present invention can be incorporated in risk installations for on-line monitoring of the concentration of *Legionella*, without the need for professional supervision, making an efficient prevention strategy for the biological risk associated with *Legionella* possible.

Example 4

Comparison of the Protective Effect Against the Non-Specific Adsorption of a Static Coating Compared to a Dynamic Coating of the Particle A comparison of the protective effect of two different types of inerting the surface of the immunomagnetic particle has been performed, on one hand, by means of the covalent bonding of a dextran-aspartic acid-aldehyde (DAA) polymer, and on the other hand, following that described by the present invention, by means of the non-covalent bonding of a protein, bovine serum albumin (BSA) and the maintenance of its concentration in excess in the microenvironment of the immunomagnetic particles, said particles previously blocked with said blocking agent.

The specified protocol was then applied separately to the two types of anti-*E. coli* immunomagnetic particles. In one of them, said particles were blocked with BSA, and in the other case, they were blocked with DAA. In all cases, an excess of BSA is maintained throughout the analysis. The protocol was applied for each type of particle with four samples of 0, 10, $10^2$, and $10^3$ cfu/ml of *E. coli*.

This comparison is performed according to the following protocol: i) adding 25 µl of a suspension of anti-*E. coli* immunomagnetic particle on 4.0 ml of the sample (all the samples with 2% BSA in 150 mM phosphate at pH 7.0); ii) gentle stirring for 15 minutes at room temperature; iii) retention of the immunomagnetic particles and evacuation of the supernatant; iv) three consecutive washings with a 150 mM phosphate buffer solution at pH 7.0 and 2% BSA, and a final washing with a 25 mM phosphate buffer solution at pH 7.0 and 2% BSA; v) resuspension of the immunomagnetic particle in 1.0 ml of a 25 mM phosphate buffer solution at pH 7.0 and 2% BSA, containing an anti-*E. coli* antibody obtained in rabbit (1/200 dilution); vi) gentle stirring for 15 minutes at room temperature; vii) three consecutive washings with a 150 mM phosphate buffer solution at pH 7.0 and 2% BSA, and a final washing with a 25 mM phosphate buffer solution at pH 7.0 and 2% BSA; viii) resuspension of the immunomagnetic particle in 1.0 ml in a 25 mM phosphate buffer solution at pH 7.0 and 2% BSA, containing an anti-rabbit antibody conjugated with peroxidase (1/1000 dilution); ix) gentle stirring for 15 minutes at room temperature; x) three consecutive washings with a 150 mM phosphate buffer solution at pH 7.0 and 2% BSA, and a final washing with a 25 mM phosphate buffer solution at pH 7.0 and 2% BSA; xi) resuspension of the immunomagnetic particle in 1.0 ml of a 5 mM ABTS solution, in a 50 mM phosphate buffer at pH 6.0, and 0.03% $H_2O_2$; and xii) reading the absorbance at 405 nm over time.

As shown in the table of FIG. 9, the immunomagnetic particles blocked with BSA and subjected to constant BSA pressure throughout the analysis as proposed by the present invention allow discriminating all the assayed concentrations of *E. coli*. However, the immunomagnetic particles blocked with DAA do not allow discriminating the assayed concentrations of *E. coli*

This suggests that DAA protects the particle from non-specific adsorption but said polymer also coats the recognition regions of the immobilized antibodies, such that it prevents the antigen-antibody interaction and accordingly the capture of *E. coli* cells.

Example 5

Effect of the Continuous Protection of the Immunomagnetic Particle Against the Non-Specific Adsorption of the Reading Molecule Said protocol was separately applied to two 25 µl aliquots of immunomagnetic particle, both initially blocked with BSA, but in a case with 1% BSA in the buffers used in the different steps of the protocol, and in another case without BSA.

It has been determined the effect of the presence of a blocking agent, bovine serum albumin (BSA), on the non-specific adsorption of the reading molecule in the immunomagnetic particle, maintaining an excess of concentration around the immunomagnetic particle for all the steps of the analysis. Said analysis is performed according to the following protocol: i) suspension of 25 µL of immunomagnetic particle with an anti-*E. coli* antibody obtained in goat, immobilized on its surface, in a volume of 1.0 ml of a 150 mM phosphate buffer, pH 7.0; ii) gentle stirring for 15 minutes at room temperature; iii) retention of the immunomagnetic particles and evacuation of the supernatant; iv) resuspension of the immunomagnetic particles in 1.0 ml of a 1/200 solution of an anti-*E. coli* antibody obtained in rabbit, in a 150 mM phosphate buffer, pH 7.0; v) gentle stirring for 30 minutes at room temperature; vi) Five consecutive washings with a 25 mM phosphate buffer solution, pH 7.0; retention of the immunomagnetic particles and evacuation of the supernatant; vii) resuspension of the immunomagnetic particles in 1.0 ml of a 1/200 solution of an anti-rabbit reading antibody, conjugated with peroxidase; viii) gentle stirring for 15 minutes at room temperature; ix) Three consecutive washings with a 25 mM phosphate buffer solution, pH 7.0; retention of the immunomagnetic particles and evacuation of the supernatant; x)

resuspension of the immunomagnetic particles in 1.0 ml of a solution of 1 mM ABTS and 0.03% $H_2O_2$.

The blocked immunomagnetic particles which were processed by means of the protocol including constant pressure of the blocking agent throughout the analysis showed a reduction of the non-specific adsorption of the reading molecule, sustained over time, with respect to the blocked immunomagnetic particles processed by means of the equivalent protocol but which does not include the blocking agent (FIG. 10).

This suggests that some blocking molecules initially adsorbed on the surface of the particles are released into the medium in the washing steps using buffers free of blocking agent and in the dilution with the sample. Accordingly, reactive groups on which the antibody conjugated with the reading molecule is adsorbed in a non-specific manner can be exposed. In these conditions, an important part of the final reading of the analysis will be due to said non-specific adsorption and the signal/noise ratio will be significantly reduced.

Therefore, to generate immunomagnetic particles which do not adsorb the reading molecule in a non-specific manner, it is not enough to block said interaction with pre-adsorption of the blocking agent on the particles; it will be necessary to maintain a sufficient concentration of said blocking agent in the microenvironment of the particle throughout the analysis in order to obtain the maximum load of blocking agent on the surface, which allows maintaining its protective effect against washing and dilution.

Example 6

Dependence of the Reading with the Presence of Active Endogenous Catalase in the *Escherichia coli* Cells Captured on the Magnetic Particles FIG. 6 shows the dependence of the rate of the reading reaction (colorimetry) with the inhibition of the catalase activity of the *Escherichia coli* cells captured on the magnetic particles from a suspension containing $1.1 \times 10^6$ cfu/ml.

Two samples are thus prepared, each of which contains a volume of 1.5 ml of a suspension of *E. coli* containing $1.1 \times 10^7$ cfu/ml on a volume of 15.0 ml of a 20.0 mM phosphate buffer solution at pH 7.0 with 1% bovine serum albumin (BSA), such that the final concentration is $1.1 \times 10^6$ cfu/ml in all the samples. A volume of 25.0 µL of magnetic particles with an anti-*E. coli* polyclonal antibody is added in each sample. The mixture is incubated under gentle stirring for 90 minutes and at room temperature. A control is prepared in the same manner, the only difference thereof with the samples is that it does not contain *E. coli*.

After incubation, the control and the samples are washed three times with a volume of 5.0 ml each time of a solution of 150 mM phosphate buffer containing 2% BSA. After the third washing, both in the control and in the samples, the pellets containing free magnetic particles and also the immunocomplexes formed between the *Escherichia coli* cells and the magnetic particles are resuspended in a volume of 1.0 ml of a 1/200 solution of an anti-*Escherichia coli* polyclonal antibody obtained in rabbit. The mixtures are incubated under gentle stirring and at room temperature for 15 minutes.

After incubation, the pellets are washed three times, each time with a volume of 5.0 ml of a 150 mM phosphate buffer solution containing 2% BSA. Then, in one of the two samples, the pellet is resuspended in a solution of 1.0 ml of 3.2 mg/ml of sodium azide in 150 mM phosphate buffer with BSA and at pH 7.0. After incubation, the pellets are thoroughly washed each time with a volume of 5.0 ml of a 150 mM phosphate buffer solution containing 2% BSA (six or more washings).

Finally, each pellet is resuspended in a volume of 1.0 ml of a solution of an anti-rabbit polyclonal antibody conjugated with peroxidase. The mixtures are incubated under gentle stirring and at room temperature for 15 minutes. After the incubation, the pellets are washed three times, each time with a volume of 5.0 ml of a 150 mM phosphate buffer solution containing 2% BSA.

In order to perform the assay for peroxidase activity, each pellet is placed in a volume of 1.0 ml of a solution of 5 mM ABTS and 50 mM phosphate buffer at pH 7.0, and 15 µl of 0.035% $H_2O_2$ are added. All the reactions were monitored for 4 minutes, taking an absorbance reading at 405 nm each minute.

Sodium azide inhibits the catalase activity present in the *Escherichia coli* cells captured on the magnetic particles. However, sodium azide can also inhibit the peroxidase conjugated with the anti-rabbit polyclonal antibody in turn bound to the anti-*Escherichia coli* polyclonal antibody obtained in rabbit bound to the surface of the captured cells, and accordingly it is very important to thoroughly wash the pellet containing the immunocaptured and incubated *Escherichia coli* cells with sodium azide before adding the solution of the antibody conjugated with the peroxidase.

The sample in which the catalase is not inhibited is depicted in FIG. 5 by the square symbol, and it has the same concentration of bacteria as the sample in which catalase activity is inhibited, and which is depicted by the circle symbol.

The results demonstrate that if the endogenous enzyme of the captured microorganism is not inhibited, said activity can compete with the reading molecule and give rise to an underestimation of the concentration of the microorganism in the sample, proportionally to the amount of viable cells of the captured microorganism.

This effect influences the volume of sample which can be used in the analysis. In order to reduce the limit of detection of the analysis, it is suitable to increase the volume of the sample such that the total number of cells of the microorganism in the sample is larger. However, this would increase the amount of endogenous enzyme that competes with the reading molecule and the probability of obtaining a false negative or an underestimation of the concentration of the microorganism would be greater.

Example 7

Improvement of the Sensitivity of the Determination of *Legionella* in Water by Means of Successive Captures During the process for the immunocapture of the microorganism of interest, in this example *Legionella*, the rate of capture decreases over time due essentially to two factors:

1) The binding points for the bacteria are increasingly less because they are being occupied (it is possible that, given the size of the bacterium, steric hindrances are also produced).

2) The concentration of free *Legionella* in the medium decreases over time and the rate of capture is reduced because there are proportionally fewer collisions.

A solution for the first point consists of increasing the concentration of magnetic particle and therefore of capturing antibody, which would provide a greater number of anchoring points for the microorganism. However, the active surface of the particle for a non-specific adsorption would also increase.

A solution for the second point consists of increasing the time of the immunocapture step and thus compensating the reduction of the rate of capture; if during this prolonged time the surface of the immunomagnetic particle is not deprotected, an increase of the signal of the sample without an increase of the non-specific signal could be expected. In an embodiment of the present invention, the immunocapture step has an overnight duration (16 hours). FIG. 12 presents the results obtained upon increasing the time of the immunocapture step from 15 minutes to 16 hours. The signal of the sample is significantly increased, but not the signal of the blank; this suggests that during this time period, the capture of the microorganism continues to occur without the immunomagnetic particles losing their protection against non-specific adsorption.

In another particular embodiment of the present invention, the determination of *Legionella* is performed by means of repetitions of the immunocapture step such that the sample is replaced with fresh sample in each step. This process consists of keeping the amount of immunomagnetic particle (and therefore of antibody and potential anchoring points) constant, subjected to one and the same volume of fresh sample in each step. The first capture is performed with a volume of 9.0 ml; the supernatant is evacuated and the capture is repeated with a new aliquot of fresh sample of 9.0 ml. This process is repeated up to three times (27.0 ml of total sample). Thus, when comparing results the influence of the concentration of *Legionella* in the medium for the capture process can be seen. FIG. 11 presents a comparison between two possible embodiments of the present invention for the determination of *Legionella* in water, according to said determination comprising a single capture (A) or several successive captures (B). This process increases the assay time by approximately 40 minutes, going from 60 to 110 minutes, but as is shown in FIG. 11, the signal of the sample increases by approximately 50%, the signal of the blank remaining unchanged.

Example 8

Discrimination Between Dead Bacteria and Live Bacteria in the Detection of *Legionella pneumophila*

Samples of different concentrations of *Legionella pneumophila* were analyzed by means of the quantitative process provided by the present invention. Furthermore, two types of sample are distinguished; samples in which the bacterium has been thermally inactivated, and samples in which such inactivation does not take place, such that the cells of the microorganism remain viable. Said viability is checked by culture, obtaining the corresponding counts.

In order to perform the assays, a volume of 9.0 ml of each of the suspensions of the bacterium, and 9.0 ml of a blank are prepared. The process described in Example 1 is applied both to the blank and to the samples. The results are presented in FIG. 13. As can be seen, the inactivated cells are not detected, whereas the viable cells are detected and the signal corresponding to each assayed suspension depends on the concentration of *Legionella pneumophila.*

This suggest that the process provided in the present invention could be used to perform a rapid assessment of the viable concentration of *Legionella* before and after a disinfection treatment in a risk installation, and it could be used to determine the effectiveness of a disinfecting treatment and the appropriateness of its application.

Therefore, it can be concluded that the present invention provides different advantages over the existing methods, which can be summarized as follows:

a) The present invention increases the sensitivity by means of a technical creation which does not involve the necessary use of nanoparticles, but rather even microparticles, achieving sensitivities of 1 cell/ml, an order of magnitude greater than the best sensitivity achieved by means of using nanoparticles.

b) This process is based on obtaining and using superparamagnetic particles, mainly microparticles, in which a preferably polyclonal antibody against the microorganism to be determined, suspended in a liquid medium the composition of which allows simultaneously minimizing the aggregation of the microspheres, minimizing non-specific adsorptions and minimizing interferences of the analyzed sample, and the concentration of which allows maintaining these effects against the dilution with the sample that will be analyzed, has been directly and covalently immobilized.

c) This makes it possible to obtain an efficient recovery of the microorganism based on its immunocapture, insofar as the probability of antigen-antibody interaction is high due to the fact that the surface of the particle exposed to the collision with the microorganism is elevated at all times and the handling of the particles is quantitative, and the probability of interaction with any other chemical or biological component present in the sample is reduced.

d) It allows performing said determination both in situ, with a semiquantitative value, and in a laboratory, with a quantitative value in a time not exceeding 1 hour by means of using a mechanical device. The process can be automated to obtain an automatic biosensor.

The invention claimed is:

1. A kit for carrying out a process for detecting and/or semi-quantifying and/or quantifying a microorganism of interest in a solution or suspension, which does not contain pre-cultured microorganisms, characterized in that it comprises:

an automated biosensor for carrying out the process in an automated manner comprising:

i) cells for the capture and labeling reaction of the microorganism of interest;

ii) cells for reading the absorbance at the selected wavelength or the fluorescence at the selected emission wavelength;

iii) an optical transducer iv) a hydraulic circuit for handling a liquid utilized in the process;

v) a microprocessor for sequential control of acquisition and analysis of a signal from the optical transducer;

vi) a computer for processing data and its communication with the microprocessor;

vii) stirring devices;

viii) magnetic retention devices; and ix) thermostatic devices the process comprising the steps of:

a) mixing a sample suspected of containing the microorganism with a first pH buffering suspension comprising at least one type of paramagnetic particles that have, bound to their surface, a capturing antibody directed against the microorganism; and at least one type of blocking agent molecule in excess on the surface of said magnetic particles bound at sites not occupied by the antibody;

b) incubating the mixture from step a) for a determined time under conditions suitable for forming microorganism-magnetic particle complexes;

c) applying a magnetic field to the mixture from step b) for separating and concentrating the microorganism-magnetic particle complexes; and subsequently evacuating supernatant;

d) resuspending the microorganism-magnetic particle complexes from step c) in a second pH buffering solution comprising at least one type of blocking molecule in excess and a reading antibody labeled with a marker;

e) incubating the solution from step d) for a determined time to form reading antibody labeled-microorganism-magnetic particle complexes;

f) applying a magnetic field for separating and concentrating the reading antibody labeled-microorganism-magnetic particle complexes formed in step e); and subsequently evacuating the supernatant;

g) washing the particle complexes from step f) to remove excess of the reading antibody, and subsequently evacuating the supernatant;

h) resuspending the reading antibody labeled-microorganism-magnetic particle complexes obtained from step g) in a liquid medium comprising a substrate for developing and/or detecting the marker, a blocking agent at a concentration that allows maintaining the adsorption equilibrium shifted towards the bound blocking molecules, and an enzyme inhibitor for inhibiting intrinsic enzymes that compete for the substrate;

i) incubating the mixture from step h) for a determined time to develop a signal from the marker; and j) detecting and quantifying the signal in step i) and relating the signal to the presence and quantity of the microorganism.

2. The kit according to claim 1, further comprising:
a reusable portable apparatus for manual use for in situ analysis wherein the apparatus comprises a support containing a base and two lateral inclined planes; a mobile shaft supporting a magnet and allowing its displacement with respect to the support; at least one clamp, and at least one cuvette resting on the base and fixed in its position by the clamp; and
a color chart for a correct interpretation of the results.

3. The kit according to claim 1, further comprising a set of reactive media or compositions wherein the set of reactive media or compositions comprises:

a) composition for capturing the microorganism of interest, comprising:
a suspension of the paramagnetic particles wherein the capturing antibody is immobilized on the surface of the paramagnetic particles by means of covalent bonding, and a blocking agent is bound to the surface of the paramagnetic particles at sites not occupied by the antibody by means of non-covalent bonding, and
a liquid medium comprising i) the blocking agent, ii) a chelating agent, iii) a surfactant, iv) a biocidal agent, and v) a bacteriostatic agent, wherein the liquid medium has high ionic strength corresponding to a phosphate buffer solution with a concentration between 90 and 500 mM;

b) labeling composition for the microorganism of interest comprising:
a reading antibody conjugated with the marker, in a solution containing i) a blocking agent and ii) an inhibitor agent for inhibiting the activity of enzymes present in the microorganism that can compete with the reading antibody, and having a medium ionic strength corresponding to a phosphate buffer solution with a concentration between 30 and 90 mM;

c) reading composition for the microorganism of interest comprising:
an oxidizable substrate for developing and/or detecting the marker, wherein the substrate is present in a solution containing a weak disodium phosphate salt for reducing the autoxidation of the substrate;

d) reading composition for the microorganism of interest comprising an oxidizing substrate for developing and/or detecting the reading reaction, wherein the substrate is present in a phosphate-citrate buffer solution;

e) a stop composition for stopping the developing of the marker, comprising a strong acid or a strong base; and f) a composition for washing the paramagnetic particles comprising a blocking agent, a surfactant and a bacteriostatic agent, with a low ionic strength corresponding to a phosphate buffer solution with a concentration between 5 and 30 mM.

4. The kit according to claim 3, characterized in that
the ionic strength of a) corresponds to a sodium phosphate buffer with a concentration between 100 and 200 mM;
the ionic strength of b) corresponds to 50 mM and pH 6.0 phosphate-citrate buffer;
the phosphate-citrate buffer solution of d) has a pH of 6.0 and a concentration of 50 mM;
the concentration of strong acid or strong base of e) is between 1 M and 5 M; and
the ionic strength of f) corresponds to a sodium phosphate buffer solution at pH 7.0 and a concentration between 20 and 30 mM.

5. The kit according to claim 3, characterized in that:
the blocking agent is a carbohydrate, a polydextran, a protein, serum albumin, milk casein, coldwater fish skin gelatin, pig skin gelatin, skimmed milk powder,
the inhibitor agent is sodium azide or triazole,
the substrate for the reading antibody, substituted peroxide or urea peroxide;
the oxidizing substrate in the phosphate-citrate buffer solution is hydrogen peroxide or urea peroxide;
the oxidizable substrate in the solution containing the weak disodium phosphate salt is ortho-phenylenediamine, 2,2'-azino-bis(3-ethylbenzoazoline-6-sulfonic acid), or 5-aminosalicylic acid;
the strong acid is hydrochloric acid, nitric acid or sulfuric acid;
the strong base is potassium hydroxide or sodium hydroxide;
the weak salt is dipotassium or disodium phosphate;
the chelating agent is 2,2'-bipyridyl, dimercaptopropanol, ethylenediaminetetraacetic acid (EDTA), ethylenedioxy-diethylene-dinitrilo-tetraacetic acid, ethyleneglycol-bis-(2-aminoethyl)-N,N,N',N'-tetraacetic acid (EGTA), nitrilotriacetic acid (NTA), ortho-phenanthroline, salicylic acid or triethanolamine (TEA);
the surfactant is a non-ionic detergent, polyethoxylated alkyl phenols, polyethoxylated fatty alcohols, polyethoxylated fatty acids, alkanolamines or condensates, or sorbitan monolaurate (Tween 20);
the bacteriostatic agent is p-nitrophenyl-di-chloroacetamido propanediol (chloramphenicol), sulfanilamide, 2,4-diamino-5-(3,4,5-trimethoxybenzyl)pyrimidine (trimethoprim), or 2-(ethylmercuriomercapto)benzoic acid sodium salt (thimerosal); and
the biocidal agent is streptomycin, neomycin, gentamicin, kanamycin, or sodium azide.

6. The kit according to claim 3, characterized in that:
a) the composition for capturing the microorganism of interest comprises spherical paramagnetic particles having a mean diameter between 0.8 and 1.1 μm, a polyclonal or monoclonal anti-*Legionella* antibody as the capturing antibody, bovine serum albumin (BSA) at a 10% concentration as the blocking agent, 0.1% ethylenediaminetetraacetic acid (EDTA) as the chelating agent, 1% sorbitan monolaurate as the surfactant, sodium azide at a concentration of 0.1% as the biocidal agent, thimerosal at a concentration of 0.01% as the bacteriostatic agent, a phosphate buffer solution with a concentration of 150 mM at pH 7.0;

b) the labeling composition for the microorganism of interest comprises a peroxidase-conjugated anti-*Legionella* antibody as the reading antibody, with i) 0.1% bovine serum albumin (BSA) as the blocking agent and ii) 0.01% triazole as the inhibitor agent in a phosphate and citrate solution with a concentration of 50 mM at pH 6.0;

c) the reading composition for the microorganism of interest comprises 0.1% 5-aminosalicylic acid as the oxidizable substrate, a weak disodium phosphate salt at a concentration of 0.1 M, at a pH between 7.5 and 8.0;

d) the reading composition for the microorganism of interest comprises hydrogen peroxide or urea peroxide as the oxidizing substrate in a phosphate-citrate buffer solution with a concentration of 50 mM at pH 6.0;

e) the stop composition for the reading reaction comprises 5 M hydrochloric acid or 1 M sulfuric acid as the strong acid and 3 M sodium hydroxide as the strong base; and f) the composition for washing the immunomagnetic particles comprises 0.1% bovine serum albumin as the blocking agent, 0.02% sorbitan monolaurate as the surfactant, and 0.01% thimerosal as the bacteriostatic agent, and a phosphate buffer solution having a concentration of 25 mM at pH 7.0.

7. The kit according to claim 1, wherein the marker is an enzyme or a fluorophore.

8. The kit according to claim 1, wherein the microorganism of interest is *Legionella*.

9. The kit according to claim 1, wherein the optical transducer is selected from a group consisting of spectrophotomer or spectrofluorometer.

10. A process for detecting and/or semi-quantifying and/or quantifying a microorganism of interest in a solution or suspension, that does not contain pre-cultured microorganisms, comprising the steps of:

a) providing the kit according to claim 1;

b) mixing a sample suspected of containing the microorganism of interest with a first pH buffering suspension comprising at least one type of paramagnetic particles that have, bound to their surface, a capturing antibody directed against the microorganism; and at least one type of blocking agent molecule in excess on the surface of said magnetic particles bound at sites not occupied by the antibody;

c) incubating the mixture from step b) for a determined time under conditions suitable for forming microorganism-magnetic particle complexes;

d) applying a magnetic field to the mixture from step c) for separating and concentrating the microorganism-magnetic particle complexes; and subsequently evacuating supernatant;

e) resuspending the microorganism-magnetic particle complexes from step d) in a second pH buffering solution comprising at least one type of blocking molecule in excess and a reading antibody labeled with a marker;

f) incubating the solution from step e) for a determined time to form reading antibody labeled-microorganism-magnetic particle complexes;

g) applying a magnetic field for separating and concentrating the reading antibody labeled-microorganism-magnetic particle complexes formed in step f); and subsequently evacuating the supernatant;

h) washing the particle complexes from step g) to remove excess of the reading antibody, and subsequently evacuating the supernatant;

i) resuspending the reading antibody labeled-microorganism-magnetic particle complexes obtained from step h) in a liquid medium comprising a substrate for developing and/or detecting the marker, a blocking agent at a concentration that allows maintaining the adsorption equilibrium shifted towards the bound blocking molecules, and an enzyme inhibitor for inhibiting intrinsic enzymes that compete for the substrate;

j) incubating the mixture from step i) for a determined time to develop a signal from the marker; and k) detecting and quantifying the signal in step j) and relating the signal to the presence and/or quantification of the microorganism.

11. The process of claim 10, characterized in that the sample is of environmental origin, food origin or obtained from biological fluids.

12. The process of claim 10, characterized in that the microorganism of interest is prokaryotic or eukaryotic.

13. The process of claim 12, characterized in that the microorganism of interest is a bacterium.

14. The process of claim 13, characterized in that the microorganism of interest is selected from the group consisting of *Enterobacteriaceae, Vibrionaceae, Bacillus, Escherichia, Streptococcus, Pseudomonas, Salmonella, Legionella, Listeria, Brettanomyces, Staphylococcus, Campilobacter,* and *Enterobacter.*

15. The process of claim 10, characterized in that the reading and/or capturing antibody is monoclonal or polyclonal.

16. The process of claim 10, characterized in that the magnetic particles are spherical and have a diameter in the range of 0.5 μm to 2 μm.

17. The process of claim 10, characterized in that the magnetic particles are chemically functionalized.

18. The process of claim 10, characterized in that during all the steps of the process, an excess concentration of at least one type of blocking molecule is maintained, such that the adsorption-desorption equilibrium is shifted towards the adsorbed molecule throughout the analysis, to prevent the non-specific adsorption on the magnetic particles, preventing false positives and false negatives.

19. The process of claim 10, characterized in that the blocking molecule is a protein or a carbohydrate.

20. The process of claim 19, characterized in that the blocking molecule is selected from the group consisting of serum albumin, milk casein, coldwater fish skin gelatin, pig skin gelatin, skimmed milk and polydextrans.

21. The process of claim 10, characterized in that the presence of the microorganism of interest is detected visually in the solution or suspension, wherein production of a color indicates presence of the microorganism.

22. The process of claim 10, characterized in that the detection sensitivity of the process is of 1 cell/ml.

23. The process of claim 10, characterized in that the result is obtained in a time less than or equal to one hour.

24. A reusable manual analysis device for detecting and/or semi-quantifying and/or quantifying microorganisms in a solution or suspension according to claim 10, comprising a support containing a base and two lateral inclined planes; a mobile shaft supporting a magnet and allowing its displacement with respect to the support; at least one fastener in the form of a clamp, and at least one cuvette resting on the base and fixed in its position by the fastener in the form of a clamp.

25. Use of the manual device according to claim 24 for detecting and/or semi-quantifying and/or quantifying microorganisms in a solution or suspension.

26. An automated biosensor for carrying out the process for detecting and/or semi-quantifying and/or quantifying microorganisms in a solution or suspension according to claim 10 comprising:
  i) cells for the capture and labeling reaction of the microorganism of interest;
  ii) cells for reading the absorbance at the selected wavelength or the fluorescence at the selected emission wavelength;
  iii) an optical transducer which, in the case of *Legionella*, consists of a spectrophotometer or spectrofluorometer;
  iv) a hydraulic circuit for handling the different liquids;
  v) a microprocessor for the sequential control of the analysis and the acquisition of a signal from the optical transducer;
  vi) a computer for processing data and its communication with the microprocessor;
  vii) stirring devices;
  viii) magnetic retention devices; and
  ix) thermostatic devices.

27. The biosensor according to claim 26, characterized in that each measurement cycle comprises analysis of a blank and analysis of a sample, the resulting absorbance value being the consequence of subtracting the signal of the blank from the signal of the sample.

28. Use of the automated biosensor according to claim 26, for on-line monitoring of concentration of a microorganism in water, based on using disposable aliquots of immunomagnetic particles for the capture of said microorganism.

29. Use of the biosensor according to claim 28, characterized in that said microorganism is selected from the group consisting of *Enterobacteriaceae*, *Vibrionaceae*, *Bacillus*, *Escherichia*, *Streptococcus*, *Pseudomonas*, *Salmonella*, *Legionella*, *Listeria*, *Brettanomyces*, *Staphylococcus*, *Campilobacter*, and *Enterobacter*.

30. The process according to claim 10, wherein the marker is an enzyme or a fluorophore.

31. The process according to claim 17, wherein the magnetic particles are chemically functionalized with $NH_2$, COOH or —OH groups.

* * * * *